United States Patent
Erickson et al.

(10) Patent No.: US 6,485,922 B1
(45) Date of Patent: Nov. 26, 2002

(54) METHODS FOR DETECTING COMPOUNDS WHICH MODULATE THE ACTIVITY OF AN LPA RECEPTOR

(75) Inventors: James Erickson, El Cerrito; J. Graham Goddard, San Francisco; Michael Kiefer, Clayton, all of CA (US)

(73) Assignee: Atairgin Technologies, Inc., Irvine, CA (US)

( * ) Notice: Subject to any disclaimer, the term of this patent is extended or adjusted under 35 U.S.C. 154(b) by 0 days.

(21) Appl. No.: 09/169,205

(22) Filed: Oct. 9, 1998

Related U.S. Application Data

(60) Provisional application No. 60/061,572, filed on Oct. 10, 1997, provisional application No. 60/096,990, filed on Aug. 18, 1998, and provisional application No. 60/098,985, filed on Sep. 2, 1998.

(51) Int. Cl.$^7$ .................. G01N 33/569; G01N 33/53
(52) U.S. Cl. .................. 435/7.31; 435/7.1; 435/7.2; 435/254.11; 530/350; 536/23.5
(58) Field of Search .................. 530/350; 536/23.5; 435/7.1, 7.2, 7.31, 254.11

(56) References Cited

U.S. PATENT DOCUMENTS

| | | | |
|---|---|---|---|
| 5,401,629 A | | 3/1995 | Harpold et al. .................. 435/6 |
| 5,482,835 A | | 1/1996 | King et al. .................. 435/6 |
| 5,620,993 A | * | 4/1997 | Patane et al. .................. 514/321 |
| 5,989,920 A | * | 11/1999 | Gerald et al. .................. 436/501 |
| 6,140,060 A | * | 10/2000 | Chun et al. .................. 435/7.1 |
| 6,255,059 B1 | * | 7/2001 | Klein et al. .................. 435/7.31 |

FOREIGN PATENT DOCUMENTS

| | | |
|---|---|---|
| CA | 2199455 | 3/1997 |
| WO | WO 95/21925 | 8/1995 |
| WO | WO 95/30012 | 11/1995 |
| WO | WO 96/39436 * | 12/1996 |
| WO | WO 97/00952 | 1/1997 |
| WO | WO 97/11159 | 3/1997 |

OTHER PUBLICATIONS

Masana et al., Database swiss–prot38, Accession No. P46628, Nov. 1, 1995.*
Moolenaar, Curr. Opin. Cell Biol., vol. 9(2), pp. 168–173, 1997 sequence of Edg–2 public availability of GenEmbl database Nov. 18, 1996.*
Ewing et al., Genomic Research, vol. 8, pp. 175–185, 1998.*
An et al., *Biochem. Biophys. Res. Comm.*, 231(3):619–622 (1997).
Hecht et al., *J. Cell Biol.*, 135(4):1071–1083 (1996).
Chambers, Jon K. et al., "A G Protein–coupled Receptor for UDP–glucose," Journal of Biological Chemistry, vol. 275, Apr. 14, 2000, pp. 10767–10771.
Klein, Christine et al., "Identification of surrogate agonists for the human FPRL–1 receptor by autocrine selection in yeast," Nature Biotechnology, vol. 16, Dec. 1998, pp. 1334–1337.
Lagane, Bernard, et al., "Role of Sterols in Modulating the Human μ–Opioid Receptor Function in *Saccharomyces cerevisiae*," Journal of Biological Chemistry, vol. 275, Oct. 27, 2000, pp. 33197–33200.
Swift, Steven, et al., "PAR1 Thrombin Receptor–G Protein Interactions," Journal of Biological Chemistry, vol. 275, Jan. 28, 2000, pp. 2627–2765.
Wilson, Shelagh, et al., "Orphan G–protein–coupled receptors: the next generation of drug targets?" British Journal of Pharmacology, (1998) 125, 1387–1392.

* cited by examiner

*Primary Examiner*—Yvonne Eyler
*Assistant Examiner*—Eileen B. O'Hara
(74) *Attorney, Agent, or Firm*—Orrick Herrington & Sutcliffe LLP

(57) ABSTRACT

The present invention provides novel methods for identifying and characterizing compounds that modulate the activity of an LPA receptor.

4 Claims, 4 Drawing Sheets

SEQUENCE LISTING

<160> NUMBER OF SEQ ID NOS: 24

<210> SEQ ID NO 1
<211> LENGTH: 1110
<212> TYPE: DNA
<213> ORGANISM: Homo sapiens
<220> FEATURE:
<221> NAME/KEY: CDS
<222> LOCATION: (10)..(1101)

<400> SEQUENCE: 1

```
ggatccatc atg gct gcc atc tct act tcc atc cct gta att tca cag ccc      51
          Met Ala Ala Ile Ser Thr Ser Ile Pro Val Ile Ser Gln Pro
            1               5                  10 cag ttc aca gcc atg aat gaa cca cag tgc ttc tac aac gag tcc att       99
Gln Phe Thr Ala Met Asn Glu Pro Gln Cys Phe Tyr Asn Glu Ser Ile
 15                  20                  25                  30 gcc ttc ttt tat aac cga agt gga aag cat ctt gcc aca gaa tgg aac      147
Ala Phe Phe Tyr Asn Arg Ser Gly Lys His Leu Ala Thr Glu Trp Asn
                 35                  40                  45 aca gtc agc aag ctg gtg atg gga ctt gga atc act gtt tgt atc ttc      195
Thr Val Ser Lys Leu Val Met Gly Leu Gly Ile Thr Val Cys Ile Phe
             50                  55                  60 atc atg ttg gcc aac cta ttg gtc atg gtg gca atc tat gtc aac cgc      243
Ile Met Leu Ala Asn Leu Leu Val Met Val Ala Ile Tyr Val Asn Arg
         65                  70                  75 cgc ttc cat ttt cct att tat tac cta atg gct aat ctg gct gct gca      291
Arg Phe His Phe Pro Ile Tyr Tyr Leu Met Ala Asn Leu Ala Ala Ala
     80                  85                  90 gac ttc ttt gct ggg ttg gcc tac ttc tat ctc atg ttc aac aca gga      339
Asp Phe Phe Ala Gly Leu Ala Tyr Phe Tyr Leu Met Phe Asn Thr Gly
 95                 100                 105                 110 ccc aat act cgg aga ctg act gtc agc aca tgg ctc ctt cgt cag ggc      387
Pro Asn Thr Arg Arg Leu Thr Val Ser Thr Trp Leu Leu Arg Gln Gly
                115                 120                 125 ctc att gac acc agc ctg acg gca tct gtg gcc aac tta ctg gct att      435
Leu Ile Asp Thr Ser Leu Thr Ala Ser Val Ala Asn Leu Leu Ala Ile
            130                 135                 140 gca atc gag agg cac att acg gtt ttc cgc atg cag ctc cac aca cgg      483
Ala Ile Glu Arg His Ile Thr Val Phe Arg Met Gln Leu His Thr Arg
        145                 150                 155 atg agc aac cgg cgg gta gtg gtg gtc att gtg gtc atc tgg act atg      531
Met Ser Asn Arg Arg Val Val Val Val Ile Val Val Ile Trp Thr Met
    160                 165                 170 gcc atc gtt atg ggt gct ata ccc agt gtg ggc tgg aac tgt atc tgt      579
Ala Ile Val Met Gly Ala Ile Pro Ser Val Gly Trp Asn Cys Ile Cys
175                 180                 185                 190 gat att gaa aat tgt tcc aac atg gca ccc ctc tac agt gac tct tac      627
Asp Ile Glu Asn Cys Ser Asn Met Ala Pro Leu Tyr Ser Asp Ser Tyr
                195                 200                 205 tta gtc ttc tgg gcc att ttc aac ttg gtg acc ttt gtg gta atg gtg      675
Leu Val Phe Trp Ala Ile Phe Asn Leu Val Thr Phe Val Val Met Val
            210                 215                 220 gtt ctc tat gct cac atc ttt ggc tat gtt cgc cag agg act atg aga      723
Val Leu Tyr Ala His Ile Phe Gly Tyr Val Arg Gln Arg Thr Met Arg
```

```
atg tct cgg cat agt tct gga ccc cgg cgg aat cgg gat acc atg atg     771
Met Ser Arg His Ser Ser Gly Pro Arg Arg Asn Arg Asp Thr Met Met
    240             245                 250 agt ctt ctg aag act gtg gtc att gtg ctt ggg gcc ttt atc atc tgc     819
Ser Leu Leu Lys Thr Val Val Ile Val Leu Gly Ala Phe Ile Ile Cys
255                 260                 265                 270 tgg act cct gga ttg gtt ttg tta ctt cta gac gtg tgc tgt cca cag     867
Trp Thr Pro Gly Leu Val Leu Leu Leu Leu Asp Val Cys Cys Pro Gln
                275                 280                 285 tgc gac gtg ctg gcc tat gag aaa ttc ttc ctt ctc ctt gct gaa ttc     915
Cys Asp Val Leu Ala Tyr Glu Lys Phe Phe Leu Leu Leu Ala Glu Phe
            290                 295                 300 aac tct gcc atg aac ccc atc att tac tcc tac cgc gac aaa gaa atg     963
Asn Ser Ala Met Asn Pro Ile Ile Tyr Ser Tyr Arg Asp Lys Glu Met
        305                 310                 315 agc gcc acc ttt agg cag atc ctc tgc tgc cag cgc agt gag aac ccc    1011
Ser Ala Thr Phe Arg Gln Ile Leu Cys Cys Gln Arg Ser Glu Asn Pro
    320                 325                 330 acc ggc ccc aca gaa ggc tca gac cgc tcg gct tcc tcc ctc aac cac    1059
Thr Gly Pro Thr Glu Gly Ser Asp Arg Ser Ala Ser Ser Leu Asn His
335                 340                 345                 350 acc atc ttg gct gga gtt cac agc aat gat cac tct gtg gtt tagctcgag  1110
Thr Ile Leu Ala Gly Val His Ser Asn Asp His Ser Val Val
                355                 360

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 2
gcgataggat ccatcatggc tgccatctct acttc                              35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 3
gcgatactcg agctaaacca cagagtgatc attgc                              35

<210> SEQ ID NO 4
<211> LENGTH: 1149
<212> TYPE: DNA
<213> ORGANISM: Homo sapiens
<220> FEATURE:
<221> NAME/KEY: CDS
<222> LOCATION: (1)..(1146)

<400> SEQUENCE: 4 atg gtg tcc act agc atc ccg gag gtt aaa gct ctc cgc agc tca gtc      48
Met Val Ser Thr Ser Ile Pro Glu Val Lys Ala Leu Arg Ser Ser Val
  1               5                  10                  15 tct gac tat ggg aac tat gat atc ata gtc cgg cat tac aac tac aca      96
Ser Asp Tyr Gly Asn Tyr Asp Ile Ile Val Arg His Tyr Asn Tyr Thr
                20                  25                  30 ggc aag ttg aac atc ggg gcg gag aag gac cat ggc att aaa ctg act     144
Gly Lys Leu Asn Ile Gly Ala Glu Lys Asp His Gly Ile Lys Leu Thr
```

-continued

| | 35 | | | | 40 | | | | | 45 | | | | |
|---|---|---|---|---|---|---|---|---|---|---|---|---|---|---|
| tca | gtg | gtg | ttc | att | ctc | atc | tgc | tgc | ttc | atc | atc | cta | gag | aat | ata | 192 |
| Ser | Val | Val | Phe | Ile | Leu | Ile | Cys | Cys | Phe | Ile | Ile | Leu | Glu | Asn | Ile |
| | 50 | | | | 55 | | | | | 60 | | | | | |

| ttt | gtc | ttg | cta | act | att | tgg | aaa | acc | aag | aag | ttc | cac | cgg | ccc | atg | 240 |
| Phe | Val | Leu | Leu | Thr | Ile | Trp | Lys | Thr | Lys | Lys | Phe | His | Arg | Pro | Met |
| 65 | | | | | 70 | | | | | 75 | | | | | 80 |

| tac | tat | ttc | ata | ggc | aac | cta | gcc | ctc | tcg | gac | cta | tta | gca | ggc | gtg | 288 |
| Tyr | Tyr | Phe | Ile | Gly | Asn | Leu | Ala | Leu | Ser | Asp | Leu | Leu | Ala | Gly | Val |
| | | | | 85 | | | | | 90 | | | | | 95 | |

| gct | tac | aca | gct | aac | ctg | ctg | ttg | tct | ggg | gcc | acc | act | tac | aag | ctc | 336 |
| Ala | Tyr | Thr | Ala | Asn | Leu | Leu | Leu | Ser | Gly | Ala | Thr | Thr | Tyr | Lys | Leu |
| | | | 100 | | | | | 105 | | | | | 110 | | |

| aca | cct | gcc | cag | tgg | ttt | ctg | cgg | gaa | ggg | agt | atg | ttt | gtg | gct | ctc | 384 |
| Thr | Pro | Ala | Gln | Trp | Phe | Leu | Arg | Glu | Gly | Ser | Met | Phe | Val | Ala | Leu |
| | | 115 | | | | | 120 | | | | | 125 | | | |

| tct | gca | tca | gtc | ttc | agc | ctc | ctt | gcc | atc | gcc | att | gag | cgc | tac | atc | 432 |
| Ser | Ala | Ser | Val | Phe | Ser | Leu | Leu | Ala | Ile | Ala | Ile | Glu | Arg | Tyr | Ile |
| | 130 | | | | | 135 | | | | | 140 | | | | |

| acc | atg | ctg | aag | atg | aaa | cta | cac | aac | ggg | agc | aac | agc | tcg | cgc | tcc | 480 |
| Thr | Met | Leu | Lys | Met | Lys | Leu | His | Asn | Gly | Ser | Asn | Ser | Ser | Arg | Ser |
| 145 | | | | | 150 | | | | | 155 | | | | | 160 |

| ttt | ctg | ctg | atc | agc | gcc | tgc | tgg | gtc | atc | tcc | ctc | atc | ctg | ggg | ggc | 528 |
| Phe | Leu | Leu | Ile | Ser | Ala | Cys | Trp | Val | Ile | Ser | Leu | Ile | Leu | Gly | Gly |
| | | | | 165 | | | | | 170 | | | | | 175 | |

| ctg | ccc | agc | atg | ggc | tgg | aac | tgc | atc | agc | tcg | ctg | tct | agc | tgc | tcc | 576 |
| Leu | Pro | Ser | Met | Gly | Trp | Asn | Cys | Ile | Ser | Ser | Leu | Ser | Ser | Cys | Ser |
| | | | 180 | | | | | 185 | | | | | 190 | | |

| acc | gtg | ctc | ccg | ctc | tac | cac | aag | cac | tat | att | ctc | ttc | tgc | acc | acc | 624 |
| Thr | Val | Leu | Pro | Leu | Tyr | His | Lys | His | Tyr | Ile | Leu | Phe | Cys | Thr | Thr |
| | | 195 | | | | | 200 | | | | | 205 | | | |

| gtc | ttc | act | ctg | ctc | ctg | ctt | tcc | atc | gcc | atc | ctc | tac | tgc | agg | atc | 672 |
| Val | Phe | Thr | Leu | Leu | Leu | Leu | Ser | Ile | Ala | Ile | Leu | Tyr | Cys | Arg | Ile |
| | 210 | | | | | 215 | | | | | 220 | | | | |

| tac | tcc | ttg | gtc | agg | act | cga | agc | cgc | cgc | ctg | acc | ttc | cgc | aag | aac | 720 |
| Tyr | Ser | Leu | Val | Arg | Thr | Arg | Ser | Arg | Arg | Leu | Thr | Phe | Arg | Lys | Asn |
| 225 | | | | | 230 | | | | | 235 | | | | | 240 |

| atc | tcc | aag | ggc | agt | cgc | agt | tct | gag | aag | tct | ctg | gcc | ttg | ttg | aag | 768 |
| Ile | Ser | Lys | Gly | Ser | Arg | Ser | Ser | Glu | Lys | Ser | Leu | Ala | Leu | Leu | Lys |
| | | | | 245 | | | | | 250 | | | | | 255 | |

| acg | gtg | atc | att | gtc | ttg | agt | gtc | ttc | att | gcc | tgc | tgg | gcc | cct | ctc | 816 |
| Thr | Val | Ile | Ile | Val | Leu | Ser | Val | Phe | Ile | Ala | Cys | Trp | Ala | Pro | Leu |
| | | | 260 | | | | | 265 | | | | | 270 | | |

| ttc | atc | cta | cta | ctg | tta | gat | gtg | ggc | tgc | aag | gcg | aag | acc | tgt | gac | 864 |
| Phe | Ile | Leu | Leu | Leu | Leu | Asp | Val | Gly | Cys | Lys | Ala | Lys | Thr | Cys | Asp |
| | | 275 | | | | | 280 | | | | | 285 | | | |

| atc | ctg | tac | aaa | gca | gag | tac | ttc | ctg | gtt | ctg | gct | gtg | ctg | aac | tca | 912 |
| Ile | Leu | Tyr | Lys | Ala | Glu | Tyr | Phe | Leu | Val | Leu | Ala | Val | Leu | Asn | Ser |
| | 290 | | | | | 295 | | | | | 300 | | | | |

| ggt | acc | aac | ccc | atc | atc | tac | act | ctg | acc | aac | aag | gag | atg | cgc | cgg | 960 |
| Gly | Thr | Asn | Pro | Ile | Ile | Tyr | Thr | Leu | Thr | Asn | Lys | Glu | Met | Arg | Arg |
| 305 | | | | | 310 | | | | | 315 | | | | | 320 |

| gcc | ttc | atc | cgg | atc | gta | tct | tgt | tgc | aaa | tgc | ccc | aac | gga | gac | tct | 1008 |
| Ala | Phe | Ile | Arg | Ile | Val | Ser | Cys | Cys | Lys | Cys | Pro | Asn | Gly | Asp | Ser |
| | | | | 325 | | | | | 330 | | | | | 335 | |

| gct | ggc | aaa | ttc | aag | agg | ccc | atc | atc | cca | ggc | atg | gaa | ttt | agc | cgc | 1056 |
| Ala | Gly | Lys | Phe | Lys | Arg | Pro | Ile | Ile | Pro | Gly | Met | Glu | Phe | Ser | Arg |
| | | | 340 | | | | | 345 | | | | | 350 | | |

| agc | aaa | tca | gac | aac | tcc | tct | cac | ccc | cag | aag | gac | gat | ggg | gac | aac | 1104 |

```
Ser Lys Ser Asp Asn Ser Ser His Pro Gln Lys Asp Asp Gly Asp Asn
            355                 360                 365 cca gag acc att atg tcg tct gga aac gtc aat tct tct tcc taa          1149
Pro Glu Thr Ile Met Ser Ser Gly Asn Val Asn Ser Ser Ser
        370                 375                 380

<210> SEQ ID NO 5
<211> LENGTH: 1137
<212> TYPE: DNA
<213> ORGANISM: Homo sapiens
<220> FEATURE:
<221> NAME/KEY: CDS
<222> LOCATION: (1)..(1137)

<400> SEQUENCE: 5 atg gca act gcc ctc ccg ccg cgt ctc cag ccg gtg cgg ggg aac gag       48
Met Ala Thr Ala Leu Pro Pro Arg Leu Gln Pro Val Arg Gly Asn Glu
  1               5                  10                  15 acc ctg cgg gag cat tac cag tac gtg ggg aag ttg gcg ggc agg ctg       96
Thr Leu Arg Glu His Tyr Gln Tyr Val Gly Lys Leu Ala Gly Arg Leu
             20                  25                  30 aag gag gcc tcc gag ggc agc acg ctc acc acc gtg ctc ttc ttg gtc      144
Lys Glu Ala Ser Glu Gly Ser Thr Leu Thr Thr Val Leu Phe Leu Val
         35                  40                  45 atc tgc agc ttc atc gtc ttg gag aac ctg atg gtt ttg att gcc atc      192
Ile Cys Ser Phe Ile Val Leu Glu Asn Leu Met Val Leu Ile Ala Ile
     50                  55                  60 tgg aaa aac aat aaa ttt cac aac cgc atg tac ttt ttc att ggc aac      240
Trp Lys Asn Asn Lys Phe His Asn Arg Met Tyr Phe Phe Ile Gly Asn
 65                  70                  75                  80 ctg gct ctc tgc gac ctg ctg gcc ggc atc gct tac aag gtc aac att      288
Leu Ala Leu Cys Asp Leu Leu Ala Gly Ile Ala Tyr Lys Val Asn Ile
                 85                  90                  95 ctg atg tct ggc aag aag acg ttc agc ctg tct ccc acg gtc tgg ttc      336
Leu Met Ser Gly Lys Lys Thr Phe Ser Leu Ser Pro Thr Val Trp Phe
            100                 105                 110 ctc agg gag ggc agt atg ttc gtg gcc ctt ggg gcg tcc acc tgc agc      384
Leu Arg Glu Gly Ser Met Phe Val Ala Leu Gly Ala Ser Thr Cys Ser
        115                 120                 125 tta ctg gcc atc gcc atc gag cgg cac ttg aca atg atc aaa atg agg      432
Leu Leu Ala Ile Ala Ile Glu Arg His Leu Thr Met Ile Lys Met Arg
    130                 135                 140 cct tac gac gcc aac aag agg cac cgc gtc ttc ctc ctg atc ggg atg      480
Pro Tyr Asp Ala Asn Lys Arg His Arg Val Phe Leu Leu Ile Gly Met
145                 150                 155                 160 tgc tgg ctc att gcc ttc acg ctg ggc gcc ctg ccc att ctg ggc tgg      528
Cys Trp Leu Ile Ala Phe Thr Leu Gly Ala Leu Pro Ile Leu Gly Trp
                165                 170                 175 aac tgc ctg cac aat ctc cct gac tgc tct acc atc ctg ccc ctc tac      576
Asn Cys Leu His Asn Leu Pro Asp Cys Ser Thr Ile Leu Pro Leu Tyr
            180                 185                 190 tcc aag aag tac att gcc ttc tgc atc agc atc ttc acg gcc atc ctg      624
Ser Lys Lys Tyr Ile Ala Phe Cys Ile Ser Ile Phe Thr Ala Ile Leu
        195                 200                 205 gtg acc atc gtg atc ctc tac gca cgc atc tac ttc ctg gtg aag tcc      672
Val Thr Ile Val Ile Leu Tyr Ala Arg Ile Tyr Phe Leu Val Lys Ser
    210                 215                 220 agc agc cgt aag gtg gcc aac cac aac aac tcg gag cgg tcc atg gca      720
Ser Ser Arg Lys Val Ala Asn His Asn Asn Ser Glu Arg Ser Met Ala
225                 230                 235                 240 ctg ctg cgg acc gtg gtg att gtg gtg agc gtg ttc atc gcc tgc tgg      768
```

```
Leu Leu Arg Thr Val Val Ile Val Val Ser Val Phe Ile Ala Cys Trp
            245                 250                 255 tcc cca ctc ttc atc ctc ttc ctc att gat gtg gcc tgc agg gtg cag         816
Ser Pro Leu Phe Ile Leu Phe Leu Ile Asp Val Ala Cys Arg Val Gln
        260                 265                 270 gcg tgc ccc atc ctc ttc aag gct cag tgg ttc atc gtg ttg gct gtg         864
Ala Cys Pro Ile Leu Phe Lys Ala Gln Trp Phe Ile Val Leu Ala Val
            275                 280                 285 ctc aac tcc gcc atg aac ccg gtc atc tac acg ctg gcc agc aag gag         912
Leu Asn Ser Ala Met Asn Pro Val Ile Tyr Thr Leu Ala Ser Lys Glu
        290                 295                 300 atg cgg cgg gcc ttc ttc cgt ctg gtc tgc aac tgc ctg gtc agg gga         960
Met Arg Arg Ala Phe Phe Arg Leu Val Cys Asn Cys Leu Val Arg Gly
305                 310                 315                 320 cgg ggg gcc cgc gcc tca ccc atc cag cct gcg ctc gac cca agc aga        1008
Arg Gly Ala Arg Ala Ser Pro Ile Gln Pro Ala Leu Asp Pro Ser Arg
                325                 330                 335 agt aaa tca agc agc agc aac aat agc agc cac tct ccg aag gtc aag        1056
Ser Lys Ser Ser Ser Ser Asn Asn Ser Ser His Ser Pro Lys Val Lys
            340                 345                 350 gaa gac ctg ccc cac aca gac ccc tca tcc tgc atc atg gac aag aac        1104
Glu Asp Leu Pro His Thr Asp Pro Ser Ser Cys Ile Met Asp Lys Asn
        355                 360                 365 gca gca ctt cag aat ggg atc ttc tgc aac tga                            1137
Ala Ala Leu Gln Asn Gly Ile Phe Cys Asn
    370                 375

<210> SEQ ID NO 6
<211> LENGTH: 1734
<212> TYPE: DNA
<213> ORGANISM: Homo sapiens
<220> FEATURE:
<221> NAME/KEY: CDS
<222> LOCATION: (85)..(1230)

<400> SEQUENCE: 6
ggcacgaggc gccgggccat gggcctcgag cccgccccga accccgcga gcccgccttg        60 tctgcggcgt gactggaggc ccag atg gtc atc atg ggc cag tgc tac tac         111
                          Met Val Ile Met Gly Gln Cys Tyr Tyr
                            1               5 aac gag acc atc ggc ttc ttc tat aac aac agt ggc aaa gag ctc agc        159
Asn Glu Thr Ile Gly Phe Phe Tyr Asn Asn Ser Gly Lys Glu Leu Ser
 10                  15                  20                  25 tcc cac tgg cgg ccc aag gat gtg gtc gtg gtg gca ctg ggg ctg acc        207
Ser His Trp Arg Pro Lys Asp Val Val Val Val Ala Leu Gly Leu Thr
                 30                  35                  40 gtc agc gtg ctg gtg ctg ctc acc aat ctg ctg gtc ata gca gcc atc        255
Val Ser Val Leu Val Leu Leu Thr Asn Leu Leu Val Ile Ala Ala Ile
             45                  50                  55 gcc tcc aac cgc cgc ttc cac cag ccc atc tac tac ctg ctc ggc aat        303
Ala Ser Asn Arg Arg Phe His Gln Pro Ile Tyr Tyr Leu Leu Gly Asn
         60                  65                  70 ctg gcc gcg gct gac ctc ttc gcg ggc gtg gcc tac ctc ttc ctc atg        351
Leu Ala Ala Ala Asp Leu Phe Ala Gly Val Ala Tyr Leu Phe Leu Met
     75                  80                  85 ttc cac act ggt ccc cgc aca gcc cga ctt tca ctt gag ggc tgg ttc        399
Phe His Thr Gly Pro Arg Thr Ala Arg Leu Ser Leu Glu Gly Trp Phe
 90                  95                 100                 105 ctg cgg cag ggc ttg ctg gac aca agc ctc act gcg tcg gtg gcc aca        447
Leu Arg Gln Gly Leu Leu Asp Thr Ser Leu Thr Ala Ser Val Ala Thr
                110                 115                 120
```

-continued

| | |
|---|---|
| ctg ctg gcc atc gcc gtg gag cgg cac cgc agt gtg atg gcc gtg cag<br>Leu Leu Ala Ile Ala Val Glu Arg His Arg Ser Val Met Ala Val Gln<br>125                         130                      135 | 495 |
| ctg cac agc cgc ctg ccc cgt ggc cgc gtg gtc atg ctc att gtg ggc<br>Leu His Ser Arg Leu Pro Arg Gly Arg Val Val Met Leu Ile Val Gly<br>      140                      145                      150 | 543 |
| gtg tgg gtg gct gcc ctg ggc ctg ggg ctg ctg cct gcc cac tcc tgg<br>Val Trp Val Ala Ala Leu Gly Leu Gly Leu Leu Pro Ala His Ser Trp<br>155                         160                      165 | 591 |
| cac tgc ctc tgt gcc ctg gac cgc tgc tca cgc atg gca ccc ctg ctc<br>His Cys Leu Cys Ala Leu Asp Arg Cys Ser Arg Met Ala Pro Leu Leu<br>170                       175                    180                185 | 639 |
| agc cgc tcc tat ttg gcc gtc tgg gct ctg tcg agc ctg ctt gtc ttc<br>Ser Arg Ser Tyr Leu Ala Val Trp Ala Leu Ser Ser Leu Leu Val Phe<br>           190                      195                    200 | 687 |
| ctc ctc atg gtg gct gtg tac acc cgc att ttc ttc tac gtg cgg cgg<br>Leu Leu Met Val Ala Val Tyr Thr Arg Ile Phe Phe Tyr Val Arg Arg<br>205                         210                      215 | 735 |
| cga gtg cag cgc atg gca gag cat gtc agc tgc cac ccc cgc tac cga<br>Arg Val Gln Arg Met Ala Glu His Val Ser Cys His Pro Arg Tyr Arg<br>      220                      225                      230 | 783 |
| gag acc acg ctc agc ctg gtc aag act gtt gtc atc atc ctg ggg gcg<br>Glu Thr Thr Leu Ser Leu Val Lys Thr Val Val Ile Ile Leu Gly Ala<br>235                         240                      245 | 831 |
| ttc gtg gtc tgc tgg aca cca ggc cag gtg gta ctg ctc ctg gat ggt<br>Phe Val Val Cys Trp Thr Pro Gly Gln Val Val Leu Leu Leu Asp Gly<br>250                         255                    260                265 | 879 |
| tta ggc tgt gag tcc tgc aat gtc ctg gct gta gaa aag tac ttc cta<br>Leu Gly Cys Glu Ser Cys Asn Val Leu Ala Val Glu Lys Tyr Phe Leu<br>           270                      275                    280 | 927 |
| ctg ttg gcc gag gcc aac tca ctg gtc aat gct gct gtg tac tct tgc<br>Leu Leu Ala Glu Ala Asn Ser Leu Val Asn Ala Ala Val Tyr Ser Cys<br>285                         290                      295 | 975 |
| cga gat gct gag atg cgc cgc acc ttc cgc cgc ctt ctc tgc tgc gcg<br>Arg Asp Ala Glu Met Arg Arg Thr Phe Arg Arg Leu Leu Cys Cys Ala<br>      300                      305                      310 | 1023 |
| tgc ctc cgc cag tcc acc cgc gag tct gtc cac tat aca tcc tct gcc<br>Cys Leu Arg Gln Ser Thr Arg Glu Ser Val His Tyr Thr Ser Ser Ala<br>315                         320                    325 | 1071 |
| cag gga ggt gcc agc act cgc atc atg ctt ccc gag aac ggc cac cca<br>Gln Gly Gly Ala Ser Thr Arg Ile Met Leu Pro Glu Asn Gly His Pro<br>330                         335                    340                345 | 1119 |
| ctg atg act cca ccc ttt agc tac ctt gaa ctt cag cgg tac gcg gca<br>Leu Met Thr Pro Pro Phe Ser Tyr Leu Glu Leu Gln Arg Tyr Ala Ala<br>           350                      355                    360 | 1167 |
| agc aac aaa tcc aca gcc cct gat gac ttg tgg gtg ctc ctg gct caa<br>Ser Asn Lys Ser Thr Ala Pro Asp Asp Leu Trp Val Leu Leu Ala Gln<br>365                         370                    375 | 1215 |
| ccc aac caa cag gac tgactgactg gcaggacaag gtctggcatg gcacagcacc<br>Pro Asn Gln Gln Asp<br>           380 | 1270 |
| actgccaggc ctccccaggc acaccactct gcccagggaa tggggctttt gggtcatctc | 1330 |
| ccactgcctg gggagtcag atggggtgca ggaatctggc tcttcagcca tctcaggttt | 1390 |
| agggggtttg taacagacat tattctgttt tcactgcgta tccttggtaa gccctgtgga | 1450 |
| ctggttcctg ctgtgtgatg ctgagggttt taaggtgggg agagataagg gctctctcgg | 1510 |
| gccatgctac ccggtatgac tgggtaatga ggacagactg tggacacccc atctacctga | 1570 |

-continued

```
gtctgattct ttagcagcag agactgaggg gtgcagagtg tgagctggga aaggtttgtg    1630
gctccttgca gcctccaggg actggcctgt ccccaataga attgaagcag tccacgggga    1690
ggggatgata caaggagtaa acctttcttt acactcaaaa aaaa                     1734
```

<210> SEQ ID NO 7
<211> LENGTH: 1059
<212> TYPE: DNA
<213> ORGANISM: Rattus sp.
<220> FEATURE:
<221> NAME/KEY: CDS
<222> LOCATION: (1)..(1056)

<400> SEQUENCE: 7

```
atg ggc ggt tta tac tca gag tac ctc aat cct gag aag gtt cag gaa      48
Met Gly Gly Leu Tyr Ser Glu Tyr Leu Asn Pro Glu Lys Val Gln Glu
 1               5                  10                  15
cac tac aat tac acc aag gag acg ctg gac atg cag gag acg ccc tcc      96
His Tyr Asn Tyr Thr Lys Glu Thr Leu Asp Met Gln Glu Thr Pro Ser
             20                  25                  30
cgc aag gtg gcc tcc gcc ttc atc atc att tta tgc tgt gcc atc gtg     144
Arg Lys Val Ala Ser Ala Phe Ile Ile Ile Leu Cys Cys Ala Ile Val
         35                  40                  45
gtg gag aac ctt ctg gtg cta atc gca gtg gcc agg aac agc aag ttc     192
Val Glu Asn Leu Leu Val Leu Ile Ala Val Ala Arg Asn Ser Lys Phe
     50                  55                  60
cac tca gcc atg tac ctg ttc ctc ggc aac ctg gca gcc tcc gac ctg     240
His Ser Ala Met Tyr Leu Phe Leu Gly Asn Leu Ala Ala Ser Asp Leu
 65                  70                  75                  80
ctg gca ggc gtg gcc ttc gtg gcc aac acc ttg ctc tcc gga cct gtc     288
Leu Ala Gly Val Ala Phe Val Ala Asn Thr Leu Leu Ser Gly Pro Val
                 85                  90                  95
acc ctg tcc tta act ccc ttg cag tgg ttt gcc cga gag ggt tca gcc     336
Thr Leu Ser Leu Thr Pro Leu Gln Trp Phe Ala Arg Glu Gly Ser Ala
            100                 105                 110
ttc atc acg ctc tct gcc tcg gtc ttc agc ctc ctg gcc att gcc atc     384
Phe Ile Thr Leu Ser Ala Ser Val Phe Ser Leu Leu Ala Ile Ala Ile
        115                 120                 125
gag aga caa gtg gcc atc gcc aag gtc aag ctc tac ggc agt gac aaa     432
Glu Arg Gln Val Ala Ile Ala Lys Val Lys Leu Tyr Gly Ser Asp Lys
    130                 135                 140
agc tgt cga atg ttg atg ctc att ggg gcc tct tgg ctg ata tcg ctg     480
Ser Cys Arg Met Leu Met Leu Ile Gly Ala Ser Trp Leu Ile Ser Leu
145                 150                 155                 160
att ctg ggt ggc ttg ccc atc ctg ggc tgg aat tgt ctg gac cat ctg     528
Ile Leu Gly Gly Leu Pro Ile Leu Gly Trp Asn Cys Leu Asp His Leu
                165                 170                 175
gag gct tgc tcc act gtg ctg ccc ctc tat gct aag cac tat gtg ctc     576
Glu Ala Cys Ser Thr Val Leu Pro Leu Tyr Ala Lys His Tyr Val Leu
            180                 185                 190
tgc gtg gtc acc atc ttc tct gtc atc tta ctg gct atc gtg gcc ttg     624
Cys Val Val Thr Ile Phe Ser Val Ile Leu Leu Ala Ile Val Ala Leu
        195                 200                 205
tac gtc cga atc tac ttc gta gtc cgc tca agc cat gcg gac gtt gct     672
Tyr Val Arg Ile Tyr Phe Val Val Arg Ser Ser His Ala Asp Val Ala
    210                 215                 220
ggt cct cag acg ctg gcc ctg ctc aag aca gtc acc atc gta ctg ggt     720
Gly Pro Gln Thr Leu Ala Leu Leu Lys Thr Val Thr Ile Val Leu Gly
225                 230                 235                 240
gtt ttc atc atc tgc tgg ctg ccg gct ttt agc atc ctt ctc tta gac     768
Val Phe Ile Ile Cys Trp Leu Pro Ala Phe Ser Ile Leu Leu Leu Asp
                245                 250                 255
tct acc tgt ccc gtc cgg gcc tgt cct gtc ctc tac aaa gcc cat tat     816
Ser Thr Cys Pro Val Arg Ala Cys Pro Val Leu Tyr Lys Ala His Tyr
            260                 265                 270
ttc ttt gcc ttc gcc acc aac tct ctg ctc aac cct gtc atc tat     864
Phe Phe Ala Phe Ala Thr Asn Ser Leu Leu Asn Pro Val Ile Tyr
        275                 280                 285
aca tgg cgt agc cgg gac ctt cgg agg gag gta ctg agg ccc ctg ctg     912
Thr Trp Arg Ser Arg Asp Leu Arg Arg Glu Val Leu Arg Pro Leu Leu
    290                 295                 300
tgc tgg cgg cag ggg aag gga gca aca ggg cgc aga ggt ggg aac cct     960
Cys Trp Arg Gln Gly Lys Gly Ala Thr Gly Arg Arg Gly Gly Asn Pro
305                 310                 315                 320
ggt cac cga ctc ctg ccc ctc cgc agc tcc agc tcc ctg gag aga ggc    1008
Gly His Arg Leu Leu Pro Leu Arg Ser Ser Ser Ser Leu Glu Arg Gly
```

```
                        325                 330                 335
ttg cat atg cct aca tcg cca aca ttt ctg gag ggc aac aca gtg gtc        1056
Leu His Met Pro Thr Ser Pro Thr Phe Leu Glu Gly Asn Thr Val Val
                    340                 345                 350
tga                                                                    1059
```

<210> SEQ ID NO 8
<211> LENGTH: 1122
<212> TYPE: DNA
<213> ORGANISM: Murinae gen. sp.
<220> FEATURE:
<221> NAME/KEY: CDS
<222> LOCATION: (1)..(1119)

<400> SEQUENCE: 8

```
atg gcc tgt aac agc aca ccc atg ggg act tac gaa cat ctg ctg ctg          48
Met Ala Cys Asn Ser Thr Pro Met Gly Thr Tyr Glu His Leu Leu Leu
 1               5                  10                  15 aat gtg agc aac act ttg gac cct ggg gac acc cca ctg tct gca ccg          96
Asn Val Ser Asn Thr Leu Asp Pro Gly Asp Thr Pro Leu Ser Ala Pro
                20                  25                  30 ctc agg atc tcg ctg gca ata atg atg ctg ctg atg atc gtg gta gga        144
Leu Arg Ile Ser Leu Ala Ile Met Met Leu Leu Met Ile Val Val Gly
            35                  40                  45 ttc ctt ggc aac acg gtg gtc tgc atc atc gtg tac cag agg cca gcc        192
Phe Leu Gly Asn Thr Val Val Cys Ile Ile Val Tyr Gln Arg Pro Ala
        50                  55                  60 atg cgt tca gct atc aac ctg ctg ctg gcc acc ttg gcc ttc tcc gac        240
Met Arg Ser Ala Ile Asn Leu Leu Leu Ala Thr Leu Ala Phe Ser Asp
 65                  70                  75                  80 atc atg ctg tct tta tgc tgc atg cca ttc acg gcc atc acc ctc atc        288
Ile Met Leu Ser Leu Cys Cys Met Pro Phe Thr Ala Ile Thr Leu Ile
                85                  90                  95 act gtt cgc tgg cat ttc ggg gac cac ttt tgt cgg ctt tca gct act        336
Thr Val Arg Trp His Phe Gly Asp His Phe Cys Arg Leu Ser Ala Thr
            100                 105                 110 ctc tat tgg ttt ttt gtc cta gag ggc gtg gcc atc ctg ctc atc att        384
Leu Tyr Trp Phe Phe Val Leu Glu Gly Val Ala Ile Leu Leu Ile Ile
        115                 120                 125 agc gtg gac cgg ttt ctc atc atc gtg cag cgt cag gac aag ctg aac        432
Ser Val Asp Arg Phe Leu Ile Ile Val Gln Arg Gln Asp Lys Leu Asn
130                 135                 140 cca cgc agg gct aag atg atc atc gcg gcc tcc tgg gtg ctg tct ttc        480
Pro Arg Arg Ala Lys Met Ile Ile Ala Ala Ser Trp Val Leu Ser Phe
145                 150                 155                 160 tgc atc tct gcg ccc tcc ttc act ggc tgg acg ttc atg gag gtg cct        528
Cys Ile Ser Ala Pro Ser Phe Thr Gly Trp Thr Phe Met Glu Val Pro
                165                 170                 175 gct cga gcc cca cag tgc gtg cta ggc tac act gag ttc cca gct gaa        576
Ala Arg Ala Pro Gln Cys Val Leu Gly Tyr Thr Glu Phe Pro Ala Glu
            180                 185                 190 cgc gcc tat gta gtg aca ctg gtg gtg gca gtg ttc ttt gct ccc ttc        624
Arg Ala Tyr Val Val Thr Leu Val Val Ala Val Phe Phe Ala Pro Phe
        195                 200                 205 ggc gtc atg ttg tgc tcc tat ctg tgc atc ctc aat acg gtg cgg aag        672
Gly Val Met Leu Cys Ser Tyr Leu Cys Ile Leu Asn Thr Val Arg Lys
    210                 215                 220 aac gct gtc cgt gtg cac aac cag tcg gac agc ctg gac ctc aga cag        720
Asn Ala Val Arg Val His Asn Gln Ser Asp Ser Leu Asp Leu Arg Gln
225                 230                 235                 240 ctg acc gga gct ggc ctg aga cgt ctc aga cgg cag cag cag cag gcc        768
Leu Thr Gly Ala Gly Leu Arg Arg Leu Arg Arg Gln Gln Gln Gln Ala
```

```
agc ctg gac ctg agt ttc aaa acc aag gcc ttc acc acc atc ctc atc         816
Ser Leu Asp Leu Ser Phe Lys Thr Lys Ala Phe Thr Thr Ile Leu Ile
        260                 265                 270 ctc ttc gtg ggc ttt tca ctc tgc tgg ctg cca cac tca gtc tac agc         864
Leu Phe Val Gly Phe Ser Leu Cys Trp Leu Pro His Ser Val Tyr Ser
                275                 280                 285 ctg ctg tct gcg ttc agc cgg cgg ttc tat tac agc gcc tcc ttc tac         912
Leu Leu Ser Ala Phe Ser Arg Arg Phe Tyr Tyr Ser Ala Ser Phe Tyr
    290                 295                 300 acc acc agc aca tgc gtc ctg tgg ctc agt tac ctc aag tct gtt ttc         960
Thr Thr Ser Thr Cys Val Leu Trp Leu Ser Tyr Leu Lys Ser Val Phe
305                 310                 315                 320 aac ccc atc gtc tac tgc tgg agg atc aag aaa ttc cgc gag gcc tgc        1008
Asn Pro Ile Val Tyr Cys Trp Arg Ile Lys Lys Phe Arg Glu Ala Cys
                325                 330                 335 ata gag ttg ctt ccc cac act ttc caa atc ctc cct aaa gtg cct gag        1056
Ile Glu Leu Leu Pro His Thr Phe Gln Ile Leu Pro Lys Val Pro Glu
                    340                 345                 350 cgg atc cag agg aaa atc cag cca agc acc atc tat gtg tgc aac gaa        1104
Arg Ile Gln Arg Lys Ile Gln Pro Ser Thr Ile Tyr Val Cys Asn Glu
        355                 360                 365 aac caa tcc gct gtc tag                                                 1122
Asn Gln Ser Ala Val
    370
```

<210> SEQ ID NO 9
<211> LENGTH: 373
<212> TYPE: PRT
<213> ORGANISM: Mus sp.

<400> SEQUENCE: 9

```
Met Ala Cys Asn Ser Thr Pro Met Gly Thr Tyr Glu His Leu Leu Leu
  1               5                  10                  15

Asn Val Ser Asn Thr Leu Asp Pro Gly Asp Thr Pro Leu Ser Ala Pro
             20                  25                  30

Leu Arg Ile Ser Leu Ala Ile Met Met Leu Leu Met Ile Val Val Gly
         35                  40                  45

Phe Leu Gly Asn Thr Val Val Cys Ile Ile Val Tyr Gln Arg Pro Ala
     50                  55                  60

Met Arg Ser Ala Ile Asn Leu Leu Leu Ala Thr Leu Ala Phe Ser Asp
 65                  70                  75                  80

Ile Met Leu Ser Leu Cys Cys Met Pro Phe Thr Ala Ile Thr Leu Ile
                 85                  90                  95

Thr Val Arg Trp His Phe Gly Asp His Phe Cys Arg Leu Ser Ala Thr
            100                 105                 110

Leu Tyr Trp Phe Phe Val Leu Glu Gly Val Ala Ile Leu Leu Ile Ile
        115                 120                 125

Ser Val Asp Arg Phe Leu Ile Ile Val Gln Arg Gln Asp Lys Leu Asn
    130                 135                 140

Pro Arg Arg Ala Lys Met Ile Ile Ala Ala Ser Trp Val Leu Ser Phe
145                 150                 155                 160

Cys Ile Ser Ala Pro Ser Phe Thr Gly Trp Thr Phe Met Glu Val Pro
                165                 170                 175

Ala Arg Ala Pro Gln Cys Val Leu Gly Tyr Thr Glu Phe Pro Ala Glu
            180                 185                 190

Arg Ala Tyr Val Val Thr Leu Val Val Ala Val Phe Phe Ala Pro Phe
```

```
            195                 200                 205
Gly Val Met Leu Cys Ser Tyr Leu Cys Ile Leu Asn Thr Val Arg Lys
        210                 215                 220
Asn Ala Val Arg Val His Asn Gln Ser Asp Ser Leu Asp Leu Arg Gln
225                 230                 235                 240
Leu Thr Gly Ala Gly Leu Arg Arg Leu Arg Arg Gln Gln Gln Gln Ala
            245                 250                 255
Ser Leu Asp Leu Ser Phe Lys Thr Lys Ala Phe Thr Thr Ile Leu Ile
        260                 265                 270
Leu Phe Val Gly Phe Ser Leu Cys Trp Leu Pro His Ser Val Tyr Ser
        275                 280                 285
Leu Leu Ser Ala Phe Ser Arg Arg Phe Tyr Ser Ala Ser Phe Tyr
        290                 295                 300
Thr Thr Ser Thr Cys Val Leu Trp Leu Ser Tyr Leu Lys Ser Val Phe
305                 310                 315                 320
Asn Pro Ile Val Tyr Cys Trp Arg Ile Lys Lys Phe Arg Glu Ala Cys
            325                 330                 335
Ile Glu Leu Leu Pro His Thr Phe Gln Ile Leu Pro Lys Val Pro Glu
        340                 345                 350
Arg Ile Gln Arg Lys Ile Gln Pro Ser Thr Ile Tyr Val Cys Asn Glu
        355                 360                 365
Asn Gln Ser Ala Val
    370

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 10
gcgcgggatc caccatgggg cccaccagcg tcccg                          35

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 11
gcgcggtcga cggaagaaga gttgacgttt cc                             32

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 12
gcgcgggatc caccatggca actgccctcc cg                             32

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: primer
```

```
<400> SEQUENCE: 13
gcgcggtcga ctcagttgca gaagatccca ttc                          33

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: primer

<400> SEQUENCE: 14
atcagcggat ccaccatggt catcatgggc cagt                         34

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 15
agttcactcg agtcagtcct gttggttggg ttg                          33

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 16
gcgcgggatc caccatgggc ggtttatact cagag                        35

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 17
gcgcggtcga ctcagaccac tgtgttgccc                              30

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 18
gcgctctaga ccaccatggc ctgtaacagc acaccc                       36

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 19
gcgcgtcgac ctagacagcg gattggtttt cg                           32

<210> SEQ ID NO 20
<211> LENGTH: 364
```

```
<212> TYPE: PRT
<213> ORGANISM: Homo sapiens

<400> SEQUENCE: 20

Met Ala Ala Ile Ser Thr Ser Ile Pro Val Ile Ser Gln Pro
1               5                   10

Gln Phe Thr Ala Met Asn Glu Pro Gln Cys Phe Tyr Asn Glu Ser Ile
        15                  20                  25                  30

Ala Phe Phe Tyr Asn Arg Ser Gly Lys His Leu Ala Thr Glu Trp Asn
                35                  40                  45

Thr Val Ser Lys Leu Val Met Gly Leu Gly Ile Thr Val Cys Ile Phe
                50                  55                  60

Ile Met Leu Ala Asn Leu Leu Val Met Val Ala Ile Tyr Val Asn Arg
            65                  70                  75

Arg Phe His Phe Pro Ile Tyr Tyr Leu Met Ala Asn Leu Ala Ala Ala
        80                  85                  90

Asp Phe Phe Ala Gly Leu Ala Tyr Phe Tyr Leu Met Phe Asn Thr Gly
    95                  100                 105                 110

Pro Asn Thr Arg Arg Leu Thr Val Ser Thr Trp Leu Leu Arg Gln Gly
                115                 120                 125

Leu Ile Asp Thr Ser Leu Thr Ala Ser Val Ala Asn Leu Leu Ala Ile
                130                 135                 140

Ala Ile Glu Arg His Ile Thr Val Phe Arg Met Gln Leu His Thr Arg
            145                 150                 155

Met Ser Asn Arg Arg Val Val Val Ile Val Ile Trp Thr Met
        160                 165                 170

Ala Ile Val Met Gly Ala Ile Pro Ser Val Gly Trp Asn Cys Ile Cys
175                 180                 185                 190

Asp Ile Glu Asn Cys Ser Asn Met Ala Pro Leu Tyr Ser Asp Ser Tyr
                195                 200                 205

Leu Val Phe Trp Ala Ile Phe Asn Leu Val Thr Phe Val Val Met Val
                210                 215                 220

Val Leu Tyr Ala His Ile Phe Gly Tyr Val Arg Gln Arg Thr Met Arg
            225                 230                 235

Met Ser Arg His Ser Ser Gly Pro Arg Arg Asn Arg Asp Thr Met Met
        240                 245                 250

Ser Leu Leu Lys Thr Val Val Ile Val Leu Gly Ala Phe Ile Ile Cys
255                 260                 265                 270

Trp Thr Pro Gly Leu Val Leu Leu Leu Asp Val Cys Cys Pro Gln
                275                 280                 285

Cys Asp Val Leu Ala Tyr Glu Lys Phe Phe Leu Leu Leu Ala Glu Phe
        290                 295                 300

Asn Ser Ala Met Asn Pro Ile Ile Tyr Ser Tyr Arg Asp Lys Glu Met
            305                 310                 315

Ser Ala Thr Phe Arg Gln Ile Leu Cys Cys Gln Arg Ser Glu Asn Pro
        320                 325                 330

Thr Gly Pro Thr Glu Gly Ser Asp Arg Ser Ala Ser Ser Leu Asn His
335                 340                 345                 350

Thr Ile Leu Ala Gly Val His Ser Asn Asp His Ser Val Val
                355                 360

<210> SEQ ID NO 21
<211> LENGTH: 382
<212> TYPE: PRT
<213> ORGANISM: Homo sapiens
```

```
<400> SEQUENCE: 21

Met Val Ser Thr Ser Ile Pro Glu Val Lys Ala Leu Arg Ser Val
  1               5                  10                  15

Ser Asp Tyr Gly Asn Tyr Asp Ile Ile Val Arg His Tyr Asn Tyr Thr
             20                  25                  30

Gly Lys Leu Asn Ile Gly Ala Glu Lys Asp His Gly Ile Lys Leu Thr
         35                  40                  45

Ser Val Val Phe Ile Leu Ile Cys Cys Phe Ile Ile Leu Glu Asn Ile
     50                  55                  60

Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
                 85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Ser Ser Arg Ser
145                 150                 155                 160

Phe Leu Leu Ile Ser Ala Cys Trp Val Ile Ser Leu Ile Leu Gly Gly
                165                 170                 175

Leu Pro Ser Met Gly Trp Asn Cys Ile Ser Ser Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Leu Ser Ile Ala Ile Leu Tyr Cys Arg Ile
    210                 215                 220

Tyr Ser Leu Val Arg Thr Arg Ser Arg Arg Leu Thr Phe Arg Lys Asn
225                 230                 235                 240

Ile Ser Lys Gly Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Ala Lys Thr Cys Asp
        275                 280                 285

Ile Leu Tyr Lys Ala Glu Tyr Phe Leu Val Leu Ala Val Leu Asn Ser
    290                 295                 300

Gly Thr Asn Pro Ile Ile Tyr Thr Leu Thr Asn Lys Glu Met Arg Arg
305                 310                 315                 320

Ala Phe Ile Arg Ile Val Ser Cys Cys Lys Cys Pro Asn Gly Asp Ser
                325                 330                 335

Ala Gly Lys Phe Lys Arg Pro Ile Ile Pro Gly Met Glu Phe Ser Arg
            340                 345                 350

Ser Lys Ser Asp Asn Ser Ser His Pro Gln Lys Asp Asp Gly Asp Asn
        355                 360                 365

Pro Glu Thr Ile Met Ser Ser Gly Asn Val Asn Ser Ser Ser
    370                 375                 380

<210> SEQ ID NO 22
<211> LENGTH: 378
<212> TYPE: PRT
```

<213> ORGANISM: Homo sapiens

<400> SEQUENCE: 22

```
Met Ala Thr Ala Leu Pro Pro Arg Leu Gln Pro Val Arg Gly Asn Glu
  1               5                  10                  15
Thr Leu Arg Glu His Tyr Gln Tyr Val Gly Lys Leu Ala Gly Arg Leu
             20                  25                  30
Lys Glu Ala Ser Glu Gly Ser Thr Leu Thr Thr Val Leu Phe Leu Val
         35                  40                  45
Ile Cys Ser Phe Ile Val Leu Glu Asn Leu Met Val Leu Ile Ala Ile
     50                  55                  60
Trp Lys Asn Asn Lys Phe His Asn Arg Met Tyr Phe Phe Ile Gly Asn
 65                  70                  75                  80
Leu Ala Leu Cys Asp Leu Leu Ala Gly Ile Ala Tyr Lys Val Asn Ile
                 85                  90                  95
Leu Met Ser Gly Lys Lys Thr Phe Ser Leu Ser Pro Thr Val Trp Phe
            100                 105                 110
Leu Arg Glu Gly Ser Met Phe Val Ala Leu Gly Ala Ser Thr Cys Ser
        115                 120                 125
Leu Leu Ala Ile Ala Ile Glu Arg His Leu Thr Met Ile Lys Met Arg
    130                 135                 140
Pro Tyr Asp Ala Asn Lys Arg His Arg Val Phe Leu Leu Ile Gly Met
145                 150                 155                 160
Cys Trp Leu Ile Ala Phe Thr Leu Gly Ala Leu Pro Ile Leu Gly Trp
                165                 170                 175
Asn Cys Leu His Asn Leu Pro Asp Cys Ser Thr Ile Leu Pro Leu Tyr
            180                 185                 190
Ser Lys Lys Tyr Ile Ala Phe Cys Ile Ser Ile Phe Thr Ala Ile Leu
        195                 200                 205
Val Thr Ile Val Ile Leu Tyr Ala Arg Ile Tyr Phe Leu Val Lys Ser
    210                 215                 220
Ser Ser Arg Lys Val Ala Asn His Asn Ser Glu Arg Ser Met Ala
225                 230                 235                 240
Leu Leu Arg Thr Val Val Ile Val Val Ser Val Phe Ile Ala Cys Trp
                245                 250                 255
Ser Pro Leu Phe Ile Leu Phe Leu Ile Asp Val Ala Cys Arg Val Gln
            260                 265                 270
Ala Cys Pro Ile Leu Phe Lys Ala Gln Trp Phe Ile Val Leu Ala Val
        275                 280                 285
Leu Asn Ser Ala Met Asn Pro Val Ile Tyr Thr Leu Ala Ser Lys Glu
    290                 295                 300
Met Arg Arg Ala Phe Phe Arg Leu Val Cys Asn Cys Leu Val Arg Gly
305                 310                 315                 320
Arg Gly Ala Arg Ala Ser Pro Ile Gln Pro Ala Leu Asp Pro Ser Arg
                325                 330                 335
Ser Lys Ser Ser Ser Asn Asn Ser Ser His Ser Pro Lys Val Lys
            340                 345                 350
Glu Asp Leu Pro His Thr Asp Pro Ser Ser Cys Ile Met Asp Lys Asn
        355                 360                 365
Ala Ala Leu Gln Asn Gly Ile Phe Cys Asn
    370                 375
```

<210> SEQ ID NO 23
<211> LENGTH: 382

```
<212> TYPE: PRT
<213> ORGANISM: Homo sapiens

<400> SEQUENCE: 23

Met Val Ile Met Gly Gln Cys Tyr Tyr
1               5

Asn Glu Thr Ile Gly Phe Phe Tyr Asn Asn Ser Gly Lys Glu Leu Ser
 10              15                  20                  25

Ser His Trp Arg Pro Lys Asp Val Val Val Ala Leu Gly Leu Thr
                30                  35                  40

Val Ser Val Leu Val Leu Leu Thr Asn Leu Leu Val Ile Ala Ala Ile
                45                  50                  55

Ala Ser Asn Arg Arg Phe His Gln Pro Ile Tyr Tyr Leu Leu Gly Asn
         60                  65                  70

Leu Ala Ala Ala Asp Leu Phe Ala Gly Val Ala Tyr Leu Phe Leu Met
     75                  80                  85

Phe His Thr Gly Pro Arg Thr Ala Arg Leu Ser Leu Glu Gly Trp Phe
 90                  95                 100                 105

Leu Arg Gln Gly Leu Leu Asp Thr Ser Leu Thr Ala Ser Val Ala Thr
                110                 115                 120

Leu Leu Ala Ile Ala Val Glu Arg His Arg Ser Val Met Ala Val Gln
                125                 130                 135

Leu His Ser Arg Leu Pro Arg Gly Arg Val Val Met Leu Ile Val Gly
         140                 145                 150

Val Trp Val Ala Ala Leu Gly Leu Gly Leu Leu Pro Ala His Ser Trp
     155                 160                 165

His Cys Leu Cys Ala Leu Asp Arg Cys Ser Arg Met Ala Pro Leu Leu
170                 175                 180                 185

Ser Arg Ser Tyr Leu Ala Val Trp Ala Leu Ser Ser Leu Leu Val Phe
                190                 195                 200

Leu Leu Met Val Ala Val Tyr Thr Arg Ile Phe Phe Tyr Val Arg Arg
                205                 210                 215

Arg Val Gln Arg Met Ala Glu His Val Ser Cys His Pro Arg Tyr Arg
                220                 225                 230

Glu Thr Thr Leu Ser Leu Val Lys Thr Val Val Ile Ile Leu Gly Ala
 235                 240                 245

Phe Val Val Cys Trp Thr Pro Gly Gln Val Val Leu Leu Leu Asp Gly
250                 255                 260                 265

Leu Gly Cys Glu Ser Cys Asn Val Leu Ala Val Glu Lys Tyr Phe Leu
                270                 275                 280

Leu Leu Ala Glu Ala Asn Ser Leu Val Asn Ala Ala Val Tyr Ser Cys
                285                 290                 295

Arg Asp Ala Glu Met Arg Arg Thr Phe Arg Arg Leu Leu Cys Cys Ala
                300                 305                 310

Cys Leu Arg Gln Ser Thr Arg Glu Ser Val His Tyr Thr Ser Ser Ala
 315                 320                 325

Gln Gly Gly Ala Ser Thr Arg Ile Met Leu Pro Glu Asn Gly His Pro
330                 335                 340                 345

Leu Met Thr Pro Pro Phe Ser Tyr Leu Glu Leu Gln Arg Tyr Ala Ala
                350                 355                 360

Ser Asn Lys Ser Thr Ala Pro Asp Asp Leu Trp Val Leu Leu Ala Gln
                365                 370                 375

Pro Asn Gln Gln Asp
                380
```

<210> SEQ ID NO 24
<211> LENGTH: 352
<212> TYPE: PRT
<213> ORGANISM: Rattus sp.

<400> SEQUENCE: 24

Met Gly Gly Leu Tyr Ser Glu Tyr Leu Asn Pro Glu Lys Val Gln Glu
 1               5                  10                  15

His Tyr Asn Tyr Thr Lys Glu Thr Leu Asp Met Gln Glu Thr Pro Ser
            20                  25                  30

Arg Lys Val Ala Ser Ala Phe Ile Ile Ile Leu Cys Cys Ala Ile Val
        35                  40                  45

Val Glu Asn Leu Leu Val Leu Ile Ala Val Ala Arg Asn Ser Lys Phe
    50                  55                  60

His Ser Ala Met Tyr Leu Phe Leu Gly Asn Leu Ala Ala Ser Asp Leu
65                  70                  75                  80

Leu Ala Gly Val Ala Phe Val Ala Asn Thr Leu Leu Ser Gly Pro Val
                85                  90                  95

Thr Leu Ser Leu Thr Pro Leu Gln Trp Phe Ala Arg Glu Gly Ser Ala
            100                 105                 110

Phe Ile Thr Leu Ser Ala Ser Val Phe Ser Leu Leu Ala Ile Ala Ile
        115                 120                 125

Glu Arg Gln Val Ala Ile Ala Lys Val Lys Leu Tyr Gly Ser Asp Lys
    130                 135                 140

Ser Cys Arg Met Leu Met Leu Ile Gly Ala Ser Trp Leu Ile Ser Leu
145                 150                 155                 160

Ile Leu Gly Gly Leu Pro Ile Leu Gly Trp Asn Cys Leu Asp His Leu
                165                 170                 175

Glu Ala Cys Ser Thr Val Leu Pro Leu Tyr Ala Lys His Tyr Val Leu
            180                 185                 190

Cys Val Val Thr Ile Phe Ser Val Ile Leu Leu Ala Ile Val Ala Leu
        195                 200                 205

Tyr Val Arg Ile Tyr Phe Val Val Arg Ser Ser His Ala Asp Val Ala
    210                 215                 220

Gly Pro Gln Thr Leu Ala Leu Leu Lys Thr Val Thr Ile Val Leu Gly
225                 230                 235                 240

Val Phe Ile Ile Cys Trp Leu Pro Ala Phe Ser Ile Leu Leu Leu Asp
                245                 250                 255

Ser Thr Cys Pro Val Arg Ala Cys Pro Val Leu Tyr Lys Ala His Tyr
            260                 265                 270

Phe Phe Ala Phe Ala Thr Leu Asn Ser Leu Leu Asn Pro Val Ile Tyr
        275                 280                 285

Thr Trp Arg Ser Arg Asp Leu Arg Glu Val Leu Arg Pro Leu Leu
    290                 295                 300

Cys Trp Arg Gln Gly Lys Gly Ala Thr Gly Arg Arg Gly Gly Asn Pro
305                 310                 315                 320

Gly His Arg Leu Leu Pro Leu Arg Ser Ser Ser Leu Glu Arg Gly
                325                 330                 335

Leu His Met Pro Thr Ser Pro Ser Phe Leu Glu Gly Asn Thr Val Val
            340                 345                 350

METHODS FOR DETECTING COMPOUNDS WHICH MODULATE THE ACTIVITY OF AN LPA RECEPTOR

This application claims priority from U.S. Provisional Application 60/061,572, filed Oct. 10, 1997, U.S. Provisional application No. 60/096,990, filed Aug. 18, 1998, and U.S. Provisional application No. 60/098,985, filed Sep. 2, 1998.

TECHNICAL FIELD

The present invention relates to methods for identifying and characterizing compounds that modulate the activity of a member of the EDG family of receptors, including EDG-1, EDG-2, EDG-3, EDG-4, and EDG-5 (gene sequences and encoded amino acid sequences shown in SEQ ID NOS. 4, 1, 5, 6, and 7, respectively), and a similar receptor named PSP-24 (gene sequence and encoded amino acid sequence shown in SEQ ID NOS. 8 and 9).

BACKGROUND

Cellular signal transduction is a fundamental mechanism whereby external stimuli that regulate diverse cellular processes are relayed to the interior of cells. Frequently, binding of a ligand to a cell-surface receptor represents the first step in a cascade of events that results in a cellular response. The ligands recognized by specific receptors include a diverse array of molecules such as peptides, deoxyribonucleotide triphosphates and phospholipids.

Research into phospholipid signaling is an area of intense scientific investigation, as more and more bioactive lipids are being identified and their actions characterized. One important addition to the growing list of lipid messengers is lysophosphatidic acid (1-acyl-2-hydroxy-sn-glycero-3-phosphate, LPA), the simplest of all glycerophospholipids. While LPA has long been known as a precursor of phospholipid biosynthesis in both eukaryotic and prokaryotic cells, only recently has LPA emerged as an intercellular signaling molecule that is rapidly produced and released by activated cells, notably platelets, to influence target cells by acting on a specific cell-surface receptor. Moolenaar (1994) *Trends Cell Biol.* 4:213–219. Besides being synthesized and processed to more complex phospholipids in the endoplasmic reticulum, LPA can be generated through the hydrolysis of pre-existing phospholipids following cell activation. The best documented example concerns thrombin-activated platelets, where LPA production is followed by its extracellular release. Eichholtz et al. (1993) *Biochem. J.* 291:677–680. Platelet LPA is formed, at least in large part, through phospholipase $A_2$ ($PLA_2$)-mediated deacylation of newly generated phosphatidic acid (PA). Gerrard and Robinson (1989) *Biochim. Biophys. Acta* 1001:282–285. Distinct PA-specific $PLA_2$ activity has been identified in platelets ($Ca^{2+}$-dependent) and in rat brain ($Ca^{2+}$-independent), but little is known about its mode of regulation. Billah et al. (1981) *J. Biol. Chem.* 256:5399–5403; and Thompson and Clark (1995) *Biochem. J.* 306:305–309.

It remains to be examined at what stage of the platelet activation response LPA is produced and how it is released into the extracellular environment. Given the wide variety of LPA responsive cell types, LPA production and release are unlikely to be restricted to platelets. Indeed, there is preliminary evidence that growth factor-stimulated fibroblasts can also produce LPA. Fukami and Takenawa (1992) *J. Biol. Chem.* 267:10988–10993. Furthermore, LPA may be formed and released by injured cells, probably due to nonspecific activation of phospholipases. Many other cell systems remain to be examined for LPA production.

In freshly prepared mammalian serum, LPA concentrations are estimated to be in the range of approximately 2–20 μM, with oleoyl- and palmitoyl-LPA being the predominant species. Tokumura et al. (1994) *Am. J. Physiol.* 267:C204–C210; and Eichholtz et al. (1993) *Biochem. J.* 291:677–680. LPA is not detectable in platelet-poor plasma, whole blood, or cerebrospinal fluid. Tigyi and Miledi (1992) *J. Biol. Chem.* 267:21360–21367. In common with long chain fatty acids, LPA binds with high affinity to serum albumin at a molar ratio of about 3:1. Tigyi et al. (1991) *J. Biol. Chem.* 266:20602–20609; Thumser et al. (1994) *Biochem. J.* 301:801–806. It is notable that serum albumin contains several other, as yet unidentified lipids (methanol-extractable) with LPA-like biological activity. Tigyi and Miledi (1992) *J. Biol. Chem.* 267:21360–21367. This raises the interesting possibility that LPA may belong to a new family of phospholipid mediators showing overlapping biological activities and acting on distinct receptors; conceivably, the ether-linked phospholipid platelet-activating factor (PAF) and the mitogenic lipid sphingosine 1-phosphate may also belong to this putative family. Zhang et al. (1991) *J. Cell Biol.* 114:155–167.

The range of biological responses to LPA is quite diverse, ranging from induction of cell proliferation to stimulation of neurite retraction and even slimemold chemotaxis, and the body of knowledge continues to grow as more and more cellular systems are tested for LPA responsiveness. Jalink et al. (1993) *Proc. Natl. Acad. Sci. U.S.A.* 90:1857–1861; Jalink et al. (1993) *Cell Growth and Differ.* 4:247–255; and Moolenaar (1995) *Curr. Opin. Cell Biol.* 7:203–210; Dyer et al. (1992) *Molec. Brain Res.* 14:293–301; Dyer et al. (1992) *Molec. Brain Res.* 14:302–309; Tigyi and Miledi (1992) *J. Biol. Chem.* 267:21360–21367.

Although its precise physiological and pathological functions in vivo remain to be explored, LPA derived from platelets has all the hallmarks of an important mediator of wound healing and tissue regeneration. Thus, in addition to acting as an autocrine stimulator of platelet aggregation, LPA stimulates the growth of fibroblasts, vascular smooth muscle cells, endothelial cells, and keratinocytes. Moolenaar (1994) *Trends Cell Biol.* 4:213–219; Jalink et al. (1994) *Biochim. Biophys. Acta* 1198:185–196; Van Corven et al. (1989) *Cell* 59:45–54; Tigyi et al. (1994) *Proc. Natl. Acad. Sci. U.S.A.* 91:1908–1912; Tokumura et al. (1994) *Am. J. Physiol.* 267:C204–C210; and Piazza et al. (1995) *Exp. Cell Res.* 216:51–64. Intriguingly, it has been observed that LPA acts as an inhibitor of eukaryotic DNA polymerase α. Murakami-Murofushi et al. (1992) *J. Biol. Chem.* 267:21512–21517. LPA also exhibits anti-mitogenic activity toward myeloma cells, presumably through a distinct receptor subtype. Tigyi et al. (1994) *Proc. Natl. Acad. Sci.* 91:1908–1912; Murakami-Murofushi et al. (1993) *Cell Structure and Function* 18:363–370.

In addition to stimulating cell growth and proliferation, LPA promotes cellular tension and cell-surface fibronectin binding, which are important events in wound repair and regeneration. Zhang et al. (1994) *J. Cell Biol.* 127:1447–1459; Kolodney et al. (1993) *J. Biol. Chem.* 268:23850–23855; and Lapetina et al. (1981) *J. Biochem.* 256:5037–5040. As a product of the blood-clotting process, LPA is a normal constituent of serum (but not platelet-poor plasma), where it is present in an albumin-bound form at physiologically relevant concentrations. Tigyi and Miledi (1992) *J. Biol. Chem.* 267:21360–21367; and Eichholtz et al. (1993) *Biochem. J.* 291:677–680.

Recently, anti-apoptotic activity has also been ascribed to LPA. PCT Application No. PCT/US94/13649. In this study, an actively proliferating cell line was rescued from serum withdrawal-induced apoptosis by LPA. In another study, evidence has been presented suggesting that LPA can suppress apoptosis in vitro as well as in ischemic organs such as heart and liver. Wu et al. (1996) *Transplantation* (in press).

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation, and infection by human immunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; Kruman et al. (1991) *J. Cell. Physiol.* 148:267–273; Ameisen and Capron (1991) *Immunol. Today* 12:102–105; and Sheppard and Ascher (1992) *J. AIDS* 5:143–147. Agents that affect the biological control of apoptosis thus have therapeutic utility in numerous clinical indications.

Cellular shrinkage, chromatin condensation, cytoplasmic blebbing, increased membrane permeability and interchromosomal DNA cleavage characterize Apoptotic cell death. Gerschenson et al. (1992) *FASEB J.* 6:2450–2455; and Cohen and Duke (1992) *Ann. Rev. Immunol.* 10:267–293. The blebs, small, membrane-encapsulated spheres that pinch off of the surface of apoptotic cells, may continue to produce superoxide radicals which damage surrounding cell tissue and may be involved in inflammatory processes.

While apoptosis is a normal cellular event, pathological conditions and a variety of injuries can also induce it. Apoptosis is involved in a wide variety of conditions, including, but not limited to, cardiovascular disease; cancer regression; immune disorders, including, but not limited to, systemic lupus erythematosus; viral diseases; anemia; neurological disorders; diabetes; hair loss; rejection of organ transplants; prostate hypertrophy; obesity; ocular disorders; stress; aging; and gastrointestinal disorders, including, but not limited to, diarrhea and dysentery. In the myocardium, apoptotic cell death follows ischemia and reperfusion.

In Alzheimer's disease, Parkinson's disease, Huntington's chorea, epilepsy, amyotrophic lateral sclerosis, stroke, ischemic heart disease, spinal cord injury and many viral infections, for example, abnormally high levels of cell death occur. In at least some of these diseases, there is evidence that the excessive cell death occurs through mechanisms consistent with apoptosis. Among these are 1) spinal cord injury, where the severing of axons deprives neurons of neurotrophic factors necessary to sustain cellular viability; 2) stroke, where after an initial phase of necrotic cell death due to ischemia, the rupture of dead cells releases excitatory neurotransmitters such as glutamate and oxygen free radicals that stimulate apoptosis in neighboring healthy neurons; and 3) HIV infection, which induces apoptosis of T-lymphocytes.

In contrast, the level of apoptosis is decreased in cancer cells, which allows the cancer cells to survive longer than their normal cell counterparts. As a result of the increased number of surviving cancer cells, the mass of a tumor can increase even if the doubling time of the cancer cells does not increase. Furthermore, the high level of expression in a cancer cell of the bcl-2 gene, which is involved in regulating apoptosis and, in some cases, necrotic cell death, renders the cancer cell relatively resistant to chemotherapeutic agents and to radiation therapy.

There is considerable evidence of plasma membrane receptors for LPA. LPA-binding proteins have been reported in mammalian tissues and labeled using a photoaffinity crosslinker derivative. Liliom et al. (1996) *Am. J. Physiol.* 270:C772–C778; Thomson et al. (1994) *Mol. Pharmacol.* 45:718–723; and van der Bend et al. (1992) *EMBO J.* 11:2495–2501. In *X. laevis* oocytes, LPA elicits oscillatory Cl$^-$ currents. Tigyi and Miledi (1992) *J. Biol. Chem.* 267:21360–21367. This current, like other effects of LPA, is consistent with a plasma membrane receptor-mediated activation of G protein-linked signal transduction pathways.

G proteins are comprised of three subunits: a guanyl-nucleotide binding $\alpha$ subunit; a $\beta$ subunit; and a $\gamma$ subunit. G proteins cycle between two forms, depending on whether GDP or GTP is bound thereto. When GDP is bound the $G_{\alpha\beta\gamma}$ protein exists as an inactive heterotrimer, the $G_{\alpha\beta\gamma}$ complex. When GTP is bound the $\alpha$ subunit dissociates, leaving a $G_{\beta\gamma}$ complex. Importantly, when a $G_{\alpha\beta\gamma}$ complex operatively associates with an activated G protein coupled receptor in a cell membrane, the rate of exchange of GTP for bound GDP is increased and, hence, the rate of dissociation of the bound the $\alpha$ subunit from the $G_{\beta\gamma}$ complex increases. This fundamental scheme of events forms the basis for a multiplicity of different cell signaling phenomena.

At least four G protein-mediated signaling pathways have been identified in the action of LPA. These are: 1) stimulation of phospholipase C and phospholipase D; 2) inhibition of adenylyl cyclase; 3) activation of Ras and the downstream Raf/MAP kinase pathway; and 4) tyrosine phosphorylation of focal adhesion proteins in concert with remodeling of the actin cytoskeleton in a Rho-dependent manner.

GTP-binding proteins fall into two broad classes of regulatory proteins; the heterotrimeric G-proteins, and small GTPases. The alpha subunit of heterotrimeric G-proteins (G$\alpha$) and the small GTPases, as typified by the proto-oncogene Ras, share certain structural homology, and cycle between an active GTP-bound state and an inactive GDP-bound state. When stimulated by an appropriate signal, G-proteins and small GTPases become activated by the binding of GTP and physically interact with effector molecules to transduce the signal to the cell. In the case of G-proteins, binding of GTP to the $\alpha$ subunit causes the low molecular weight G$\alpha$ to dissociate from the G$\beta\gamma$ dimer where either G$\alpha$ or G$\beta\gamma$ can act as the signal transducer. An intrinsic GTPase activity hydrolyses GTP to GDP and thus attenuates the signal. Ancillary proteins collectively known as exchange factors are responsible for replacing GDP for GTP and reactivating the GTP-binding protein. Heterotrimeric G-protein coupled receptors are a special class of receptors. It is estimated that G-protein coupled receptors comprise 0.1% of the human genome (including olfactory and visual receptors) which could place the number of different receptors in the thousands. The common structural feature of these receptors are seven hydrophilic membrane spanning domains. Based on the three dimensional model of bacterial rhodopsin, it is predicted that the receptors would form a barrel shaped structure with the ligand binding domains being the extracellular loops and/or the transmembrane domains.

Recently, three putative receptors for LPA have been identified suggesting that functionally different LPA receptors may exist that dictate the particular cellular response of LPA. Hecht, J. H., et al. (1996) J. Cell. Biol. 135(4), 1071–1083; Macrae, A. D., et al. (1996) Mol. Brain. Res. 42, 245–254; An, S., et al. (1997) Biochm. Biophys. Res. Com. 231, 619–622; Guo, Z., et al. (1996) Proc. Natl. Acad. Sci. USA 93, 14367–14372; An, et al., J. Biol. Chem. (1998). Most cell types respond to LPA making it difficult to characterize the receptor dependency of a particular response to LPA since the response cannot be solely attributed to a single LPA receptor. In particular, it is difficult to assess ligand binding specificity of an LPA receptor without a naive cell line because other lipid receptors may exist with overlapping ligand specificity. Therefor, the yeast *Saccharomyces cerevisiae* was used to study the human LPA receptor EDG-2 (or Vzg-1). *S. cerevisiae* contain no endogenous LPA receptors and is therefore a potentially useful organism in which to functionally express LPA receptors and analyze their ligand specificity. Other mammalian receptors have been functionally expressed in Saccharomyces including the sommatostatin receptor. (Price, L. A., et al. (1995) Mol. Cell. Biol. 15(11), 6188–6195), the A2a adenosine receptor (Price, L. A., et al. (1996) Mol. Pharmacol. 50(4), 829–837) and the β2-adrenergic receptor (King, K., et al., (1990) Science 250, 121–123).

FIG. 1 shows a detailed schematic of the yeast pheromone-inducible MAP Kinase cascade. Saccharomyces contains a single heterotrimeric G-protein that is activated by mating factor binding to a specific receptor. Blumer, K. J., and Thorner, J. (1990) Proc. Natl. Acad. Sci. USA 87, 4363–4367. Upon stimulation by an occupied receptor, the α subunit of the heterotrimeric G protein (Gα, the GPA1 gene product (Dietzel, C., and Kurjan, J. (1987) Cell 50, 1001–1010; Miyajima, I., et al. (1987) Cell 50, 1011–1019) becomes bound to GTP and dissociates from the βγ dimer. In yeast, it is the βγ dimer that transduces the signal to Ste 11 (the MEKK equivalent (Lange-Carter, C. A., et al. (1993) *Science* 260, 315–319)) and Ste7 (the MEK equivalent (Neiman, A. M., and Herskowitz, I. (1994) Proc. Natl. Acad. Sci. USA 91, 3398–3402)). The active GTP-bound version of Gα is inactivated by hydrolysis of GTP to GDP at which time, Gα can re-associate with Gβγ and attenuates the signal (Blinder, D., and Jenness, D. D. (1989) *Mol. Cell. Biol.* 9, 3720–3726; Cole, G., (1990) *Mol. Cell. Biol.* 10(510–517); Dietzel, C., and Kurjan, J. (1987) *Cell* 50, 1001–1010; Miyajima, I., et al. (1987) *Cell* 50, 1011–1019). Like the mammalian MAP kinase, the yeast MAP kinases Fus1 and Kss1 activate a transcriptional activator, the STE12 gene product (Elion, E. A., et al. (1994) *Mol. Biol. Cell* 4, 495–510). Activated Ste12 in turn activates the transcription of several mating-inducible genes such as FUS1 (Elion, E. A., et al. (1991) *Cold Spring Harbor Symp. Quant. Biol.* 56, 41–49; Peter, M., et al. (1993) *Cell* 73, 747–760). To study the EDG-2 receptor using the yeast pheromone response pathway system, a strain carrying a mutation in the FAR1 gene was used. This mutation has the effect of uncoupling the MAP kinase cascade from cell cycle arrest allowing the yeast to continue growing during MAP kinase activation (Peter, M., et al. (1993) *Cell* 73, 747–760; Peter, M., and Herskowitz, I. (1994) Science 265, 1228–1231). Secondly, a mutationally inactivated SST2 gene was created to increase the sensitivity of the strain to G-protein activation. The SST2 gene encodes a GTPase activating protein (GAP) for the Gα subunit (the GPA1 gene product) (Dohlman, H. G., et al. (1996) *Mol. Cell. Biol.* 16(9), 5194–5209). By inactivating the SST2 gene product, Gα remains in the GTP-bound state longer and thus increases the steady-state concentration of the signal transducing βγ dimer. Finally, to quantify the response, the bacterial lacZ gene was fused to the mating inducible FUS1 promoter to create a reporter gene.

The ubiquitous presence of the response elicited by LPA in almost every cell line tested, combined with the amphiphilic character of LPA that makes radioligand binding assays extremely difficult, has presented considerable difficulties in the molecular cloning of its receptors. In view of the potential physiological significance of LPA receptors in terms of wound healing, cell regeneration and cell proliferation and apoptosis, there is a need for drug screening assays exhibiting increased specificity that facilitate the search for agonists, inverse agonists, or antagonists of LPA, as well as methods for screening analogues of LPA to determine their ability to activate EDG-2, for elucidating the pharmacological properties of these proteins.

The present invention addresses this need. Herein are described methods of screening for agonists or antagonists of EDG-1, EDG-2, EDG-3, EDG-4, and EDG-5, as well as methods of counter screening for agonists or antagonists that are specific for only one of these EDG receptors.

All references cited herein are incorporated by reference in their entirety.

SUMMARY OF THE INVENTION

Methods of screening for pharmaceutical agents that stimulate, as well as pharmaceutical agents that inhibit, EDG-1, EDG-2, EDG-3, EDG-4, and EDG-5 activity are provided.

The present invention encompasses a method for identifying compounds which modulate the activity of any of the EDG receptors, comprising the steps of: a) contacting recombinant host cells, modified to contain the DNA of SEQ. ID. NO. 1, 4, 5, 6, 7 or 8, which is operably linked to control sequences for expression, with at least one compound or signal whose ability to modulate the activity of the EDG receptor is sought to be determined, and b) analyzing the cells for a difference in functional response mediated by said receptor. More specifically, the present invention encompasses contacting said cells with at least one composition whose ability to modulate the activity of said receptor is sought to be determined, and monitoring said cells for a change in the level of a particular signal associated with activation of the EDG receptor. EDG receptors encompassed by the present invention include EDG-1, EDG-2, EDG-3, EDG-4, and EDG-5. An additional receptor encompassed by the present invention is PSP-24, a receptor of LPA discovered in mice, which can be used as a screen to evaluate the specificity of a particular ligand for any of the EDG family of receptors. For purposes of the present discussion, PSP-24 shall be encompassed by the expressions "EDG family of receptors" and "EDG related receptors, because it has similarities, including being an LPA receptor.

Additionally, the present invention contemplates a method for modulating the signal transduction activity of the EDG receptor, comprising contacting said receptor with an effective amount of at least one compound identified by the method described above.

The present invention also encompasses an agonist, antagonist, inverse agonist, or allosteric modulator identified by the above methods.

In an alternative embodiment, the present invention encompasses a method for detecting an agonist, antagonist, inverse agonist, or allosteric modulator of an EDG receptor having activity comprising the steps of: a) exposing a compound to an EDG receptor coupled to a response pathway, under conditions and for a time sufficient to allow interaction of the compound with the EDG receptor and an associated response through the pathway, and b) detecting an increase or a decrease in the stimulation of the response pathway resulting from the interaction of the compound with the EDG receptor, relative to the absence of the tested compound and therefrom determining the presence of an agonist, antagonist, inverse agonist, or allosteric modulator.

In yet another embodiment, the present invention encompasses a method for detecting an LPA agonist, antagonist, inverse agonist, or allosteric modulator of LPA receptor comprising the steps of a) exposing a compound to the EDG-2 receptor coupled to a response pathway, under conditions and for a time sufficient to allow interaction of the compound with the EDG-2 receptor and an associated response through the pathway, and b) detecting an increase or a decrease in the stimulation of the response pathway resulting from the interaction of the compound with the EDG-2 receptor, relative to the absence of the tested compound and therefrom determining the presence of an agonist, antagonist, inverse agonist, or allosteric modulator.

In yet another embodiment, the invention encompasses a method for detecting inverse agonists of LPA, comprising the steps of a) exposing a compound and LPA to the EDG-2 receptor coupled to a response pathway, under conditions and for a time sufficient to allow interaction of LPA with the EDG-2 receptor and an associated response through the pathway, and b) detecting an increase or a decrease in the stimulation of the response pathway, relative to the absence of the tested compound and therefrom determining the presence of an inverse agonist of LPA. In yet another embodiment of the present invention, a method of detecting compounds that modulate the interaction between a ligand of an EDG related receptor and the EDG related receptor is encompassed, comprising: exposing a labeled ligand of an EDG related receptor to a cell expressing said EDG related receptor; exposing a labeled compound that is believed to interact with an EDG related receptor to said cell, and detecting a change in the amount of labeled ligand bound to said cell.

MODES FOR CARRYING OUT THE INVENTION

Figure 1:
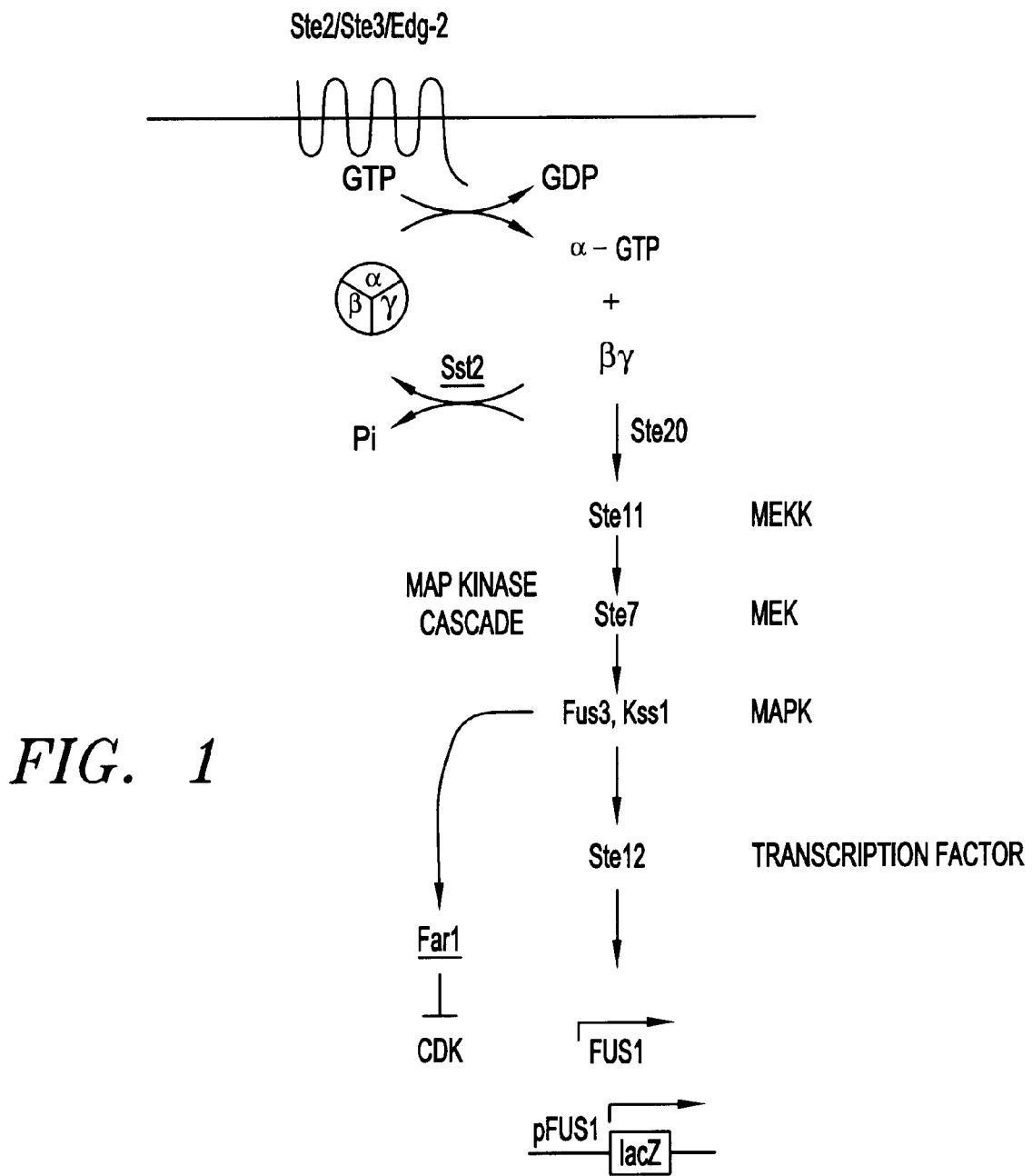
FIG. 1 shows a schematic of the yeast pheromone-inducible MAP Kinase cascade. Components of this pathway (SST2 and FAR1) that were genetically inactivated by mutation are identified by underlines.

The present invention encompasses methods for detecting substances that modulate EDG receptor activity. Additionally, the present invention encompasses compositions comprising a host organism that does not contain endogenous LPA receptor and that has been transfected with an EDG receptor. EDG receptors encompassed by the present invention include EDG-1 (SEQ ID NO. 21), EDG-2 (SEQ ID NO. 20), EDG-3 (SEQ ID NO. 22), EDG-4 (SEQ ID NO. 23), and EDG-5 (SEQ ID NO. 24). An additional receptor encompassed by the present invention is the murine receptor PSP-24 (SEQ ID NO. 9), which can be used in a screen to evaluate the specificity of a particular ligand for any of the EDG family of receptors.

The edg-2 gene product, a lysophosphatidic acid (LPA) receptor, also reported as vzg-1, couples to the yeast heterotrimeric G-protein and activates a MAP kinase cascade-dependent reporter. The response to LPA can be quantitated by using a reporter gene, including, without limitation, the lacZ gene or the luc gene fused to the FUS1 promoter, a mating pheromone-inducible gene promoter, the HIS3 gene, or any other gene that can genetically compliment an auxotropic growth mutation. The yeast strain used is able to grow in the presence of activated G-protein due to a mutation in the FAR1 gene. This mutation has the phenotypic effect of uncoupling G-protein/map kinase activation from cell cycle arrest.

The following definitions are for the purpose of clarifying the terms used herein, and are not meant to be limiting.

Vectors useful for practicing the present invention include plasmids, viruses (including phage), and integratable DNA fragments (i.e., fragments integratable into the host genome by homologous recombination). The vector may replicate and function independently of the host genome, as in the case of a plasmid, or may integrate into the genome itself, as in the case of an integratable DNA fragment. Suitable vectors will contain replicon and control sequences that are derived from species compatible with the intended expression host. For example, a promoter operable in a host cell is one which binds the RNA polymerase of that cell, and a ribosomal binding site operable in a host cell is one which binds the endogenous ribosomes of that cell.

DNA regions are "operably" associated when they are functionally related to each other. For example: a promoter is operably linked to a coding sequence if it controls the transcription of the sequence; a ribosome binding site is operably linked to a coding sequence if it is positioned so as to permit translation.

Heterologous DNA sequences are expressed in a host by means of an expression vector. An expression vector is a replicable DNA construct in which a DNA sequence encoding the heterologous DNA sequence is operably linked to suitable control sequences capable of effecting the expression of a protein or protein subunit coded for by the heterologous DNA sequence in the intended host. Generally, control sequences include a transcriptional promoter, an optional operator sequence to control transcription, a sequence encoding suitable mRNA ribosomal binding sites, and (optionally) sequences which control the termination of transcription and translation.

Transformed host cells of the present invention are cells which have been transformed or transfected with the vectors constructed using recombinant DNA techniques and express the protein or protein subunit coded for by the heterologous DNA sequences.

A variety of yeast cultures, and suitable expression vectors for transforming yeast cells, are known. See, e.g., U.S. Pat. Nos. 4,745,057; 4,797,359; 4,615,974; 4,880,734; 4,711,844; and 4,865,989. *Saccharomyces cerevisiae* is the most commonly used among the yeast, although a number of other strains are commonly available. See, e.g., U.S. Pat. No. 4,806,472 (*Kluveromyces lactis* and expression vectors therefor); U.S. Pat. No. 4,855,231 (*Pichia pastoris* and expression vectors therefor). Also, any species of Candida can be used. Yeast vectors may contain an origin of replication from the 2 micron yeast plasmid or an autonomously replicating sequence (ARS), a promoter, DNA encoding the heterologous DNA sequences, sequences for polyadenylation and transcription termination, and a selection gene. An exemplary plasmid is YRp7, (Stinchcomb et al., Nature 282, 39 (1979); Kingsman et al., Gene 7, 141 (1979); Tschemper et al., Gene 10, 157 (1980)). This plasmid contains the trp1 gene, which provides a selection marker for a mutant strain of yeast lacking the ability to grow in tryptophan, for example ATCC No. 44076 or PEP4-1 (Jones, Genetics 85, 12 (1977)). The presence of the trp1 lesion in the yeast host cell genome then provides an effective environment for detecting transformation by growth in the absence of tryptophan.

Suitable promoting sequences in yeast vectors include, but are not limited to, the promoters for metallothionein, 3-phosphoglycerate kinase (Hitzeman et al., J. Biol. Chem. 255, 2073 (1980) or other glycolytic enzymes (Hess et al., J. Adv. Enzyme Reg. 7, 149 (1968); and Holland et al., Biochemistry 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization.

In constructing suitable expression plasmids, the termination sequences associated with these genes may also be ligated into the expression vector 3' of the heterologous coding sequences to provide polyadenylation and termination of the mRNA.

A "reporter gene" is a gene that is operably linked to control sequences for expression of a gene of interest, and that encodes a gene product that can be detected for the purpose of evaluating expression of the associated gene of interest.

The "active state" of a receptor is the state at which the ligand that stimulates the receptor can bind to activate a signaling pathway controlled by the receptor.

An "EDG receptor agonist" is defined herein as a composition that is capable of combining with the active state of an EDG receptor to up-regulate a signaling pathway controlled by an the receptor. An "EDG antagonist" is defined herein as a composition that is capable of combining with the EDG receptor in either the active or inactive state, thereby impeding the biological action of the receptor. An "inverse agonist" of EDG is defined herein as a composition that is capable of combining with the inactive state of an EDG receptor to down-regulate a signaling pathway controlled by the receptor.

A composition that "modulates" the activity of an EDG receptor is defined herein as a composition that is capable of evoking a change in the functional response mediated by said receptor.

As used herein, the terms "purified" or "isolated" are intended to refer to a molecule used in the present invention in an enriched or pure form obtainable from a natural source or by means of genetic engineering or synthetic chemistry. The purified protein, DNA or RNA of the invention may be useful in ways that the protein, DNA and RNA as they naturally occur are not, such as identification of compounds selectively modulating the expression or the activity of the EDG-2 of the invention.

The isolated polypeptide and polypeptide fragments of an EDG means the EDG which is free of one or more components of its natural environment. Purified EDG includes purified EDG in recombinant cell culture. The enriched form of the receptor refers to a preparation containing said receptor in a concentration higher than natural, or in a cell where it is not found under native conditions e.g., a cellular membrane fraction comprising said receptor. If the receptor is in a pure form it is substantially free from other macromolecules, particularly from naturally occurring proteinaceous contamination. If desired, the receptor may be solubilized. Preferably, the receptor of the invention is in an active state meaning that it has both ligand binding and signal transduction activity. Receptor activity is measured according to methods known in the art, e.g., using a binding assay or a functional assay, e.g., an assay as described below.

The invention is further intended to encompass variants of the receptor of the invention. For example, a variant of an EDG receptor of the invention is a functional equivalent of said receptor. A functional equivalent is a protein displaying a physiological profile essentially identical to the profile characteristic of the particular member of the EDG family of receptors having the amino acid sequence set forth in SEQ ID NOS: 20, 21, 22, 23, 24 and 25. The physiological profile in vitro and in vivo includes receptor effector function, electrophysiological and pharmacological properties, e.g., selective interaction with agonists or antagonists. Exemplary functional equivalents may be amino acid mutants including those having amino acid deletions, substitutions or insertions, and glycosylation variants. Functional equivalents may also include EDG receptors from a different organism. The present invention also encompasses methods for comparing the agonist profile of other EDG related receptors such as EDG-1 (Lee, M.-J., et al. (1996) *J. Biol. Chem.* 271 (19), 11272–11279; Hla, T., and Maciag, T. (1990) *J. Biol. Chem.* 265(16), 9308–9313), EDG-3 (Yamaguchi, F., et al. (1996) *Biochem. Biophys. Res. Comm.* 227, 608–614) and H218 (Okazaki, H., et al. (1993) *Biochem. Biophys. Res. Com.* 190, 1104–1109; MacLennan, A. J., et al. (1994) *Mol. Cell. Neurosci.* 5, 201–209) as well as the Xenopus high-affinity LPA receptor, PSP-24 (Guo, Z., et al. (1996) *Proc. Natl. Acad. Sci. USA* 93, 14367–14372).

Covalent derivatives include, for example, aliphatic esters or amides of a receptor carboxyl group, O-acyl derivatives of hydroxyl group containing residues and N-acyl derivative of amino group containing residues. Such derivatives can be prepared by linkage of functionalities to reactable groups which are found in the side chains and at the N- and C-terminus of the receptor protein. Polypeptides of this invention may be modified post-translationally (e.g., acetylation or phosphorylation).

The invention also encompasses methods wherein an EDG receptor is conjugated to a label capable of producing a detectable signal or other functional moieties. Suitable labels include, but are not limited to, radionuclides, enzymes, substrates, cofactors, inhibitors, fluorescent dyes, chemiluminescent dyes, bioluminescent compounds and magnetic particles.

A protein for use in the invention is obtainable from a natural source, e.g., by isolation, by chemical synthesis or by recombinant techniques.

The invention further provides a method for expressing the EDG receptors in host cells. Suitable host cells producing the receptor of the invention are multiplied in vitro or in vivo. Preferably, the host cells are transformed (transfected) with a hybrid vector comprising an expression cassette comprising a promoter and an edg DNA sequence. Subsequent to expression of the edg gene under control of the promoter, the specific EDG protein may be recovered. Recovery comprises, e.g., isolating the host cells comprising the receptor, e.g., from the culture broth.

The term "functional" or "biologically active", when used herein as a modifier of an EDG, refers to a polypeptide that is able to produce one or more of the functional characteristics exhibited by that specific native EDG. In one embodiment, functional means capable of binding its specific EDG ligand. In another embodiment, functional means that a signal is transduced as a consequence of binding of a ligand.

Suitable host cells include eukaryotic cells, e.g., animal cells, plant cells and fungi, and prokaryotic cells, such as Gram-positive and Gram-negative bacteria, e.g., *Escheria coli*.

Isolated polynucleotides (or nucleic acids) encoding a polypeptide substantially identical to an EDG protein or portions thereof are designated edg. The term polynucleotide as used herein, may be DNA or RNA, either coding or noncoding strands, edg cDNA, genomic DNA and synthetic or semi-synthetic DNAs and RNAs.

The invention includes modifications to edg DNA such as deletions, substitutions and additions particularly in the non-coding regions of genomic DNA. Such changes are useful to facilitate cloning and modify gene expression in methods of the present invention.

Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses methods using functionally equivalent variants and derivatives of a particular edg which may enhance, decrease or not significantly affect the properties of the resultant EDG. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties, such as its ability to bind to LPA or analogs thereof.

An EDG is preferably incorporated into a vector (a virus, phage, or plasmid) which can be introduced by transfection or infection into a cell. The vector preferably includes one or more expression control sequences, in which case the cell transfected by the vector is capable of expressing the polypeptide. By "isolated DNA" is meant a single- or double-stranded DNA that is free of the genes that, in the naturally occurring genome of the animal from which the isolated DNA is derived, flank the edg gene. The term therefore includes, for example, either or both strands of an edg cDNA or an allelic variant thereof; a recombinant DNA which is incorporated into a vector, into an autonomously replicating plasmid or virus, or into the genomic DNA of a prokaryotic or eukaryotic cell; or a genomic DNA fragment (e.g., produced by PCR or restriction endonuclease treatment of human or other genomic DNA). The term also includes a recombinant DNA that is part of a hybrid gene encoding additional polypeptide sequence.

Stringent conditions for both DNA/DNA and DNA/RNA hybridization assays are as described by Sambrook et al., *Molecular Cloning, A Laboratory Manual*, 2nd Ed., Cold Spring Harbor Laboratory Press, Cold Spring Harbor, N.Y., 1989, herein incorporated by reference. For example, see page 7.52 of Sambrook et al.

Given the guidance of the present invention, the nucleic acids used in the invention are obtainable according to the methods well known in the art.

For example, a DNA used in the invention is obtainable by chemical synthesis, by recombinant DNA technology or by PCR. Preparation by recombinant DNA technology may involve screening a suitable cDNA or genomic library. A suitable method for preparing a DNA or of the invention may, e.g., comprise the synthesis of a number of oligonucleotides, their amplification by PCR methods, and their splicing to give the desired DNA sequence. Suitable libraries are commercially available or can be prepared from individual tissues or cell lines.

For an individual receptor related to an EDG, the expression pattern in different tissues may vary. Thus, in order to isolate cDNA encoding a particular EDG-related receptor, it is advantageous to screen libraries prepared from different suitable tissues or cells. As a screening probe, there may be employed a DNA or RNA comprising substantially the entire coding region of the edg or a suitable oligonucleotide probe based on said DNA. A suitable oligonucleotide probe (for screening involving hybridization) is a single stranded DNA or RNA that has a sequence of nucleotides that includes at least 14 contiguous bases that are the same as (or complementary to) any 14 or more contiguous bases set forth in SEQ ID NO:1, 4, 5, 6, 7 or 8, and preferably at least 18 contiguous bases that are the same as any 18 or more contiguous bases set forth in SEQ ID NO:1, 4, 5, 6, 7 or 8. The probe may be labeled with a suitable chemical moiety for ready detection. The nucleic acid sequences selected as probes should be of sufficient length and be sufficiently unambiguous so that false positive results are minimized.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labeled with suitable label means for ready detection upon hybridization. For example, a suitable label means is a radiolabel. The preferred method of labeling a DNA fragment is by incorporating $^{32}$P-labeled α-dATP with the Klenow fragment of DNA polymerase in a random priming reaction, as is well known in the art. Oligonucleotides are usually end-labeled with $^{32}$P-labeled γ-ATP and polynucleotide kinase. However, other methods (e.g., non-radioactive) may also be used to label the fragment or oligonucleotide, including, e.g., enzyme labeling and biotinylation.

After screening the library, e.g., with a portion of DNA including substantially the entire edg gene or a suitable oligonucleotide based on a portion of said DNA, positive clones are identified by detecting a hybridization signal; the identified clones are characterized by restriction enzyme mapping and/or DNA sequence analysis, and then examined, e.g., by comparison with the sequences set forth herein, to ascertain whether they include a full length edg gene (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones can be identified by comparison with the DNAs and deduced amino acid sequences provided herein.

It is envisaged that the nucleic acid of the invention can be readily modified by nucleotide substitution, nucleotide deletion, nucleotide insertion or inversion of a nucleotide stretch, and any combination thereof. Such modified sequences can be used to produce a mutant EDG that differs from the receptors found in nature. Mutagenesis may be predetermined (site-specific) or random. A mutation that is not a silent mutation should not place sequences out of reading frames and preferably will not create complementary regions that could hybridize to produce secondary mRNA structures such as loops or hairpins.

The edg cDNA or genomic DNA can be incorporated into vectors for transfection of a host cell. Furthermore, the invention concerns a recombinant DNA which is a hybrid vector comprising at least one of the above mentioned genes.

The hybrid vectors of the invention comprise an origin of replication or an autonomously replicating sequence, one or more dominant marker sequences and, optionally, expression control sequences, signal sequences and additional restriction endonuclease sites.

Preferably, the hybrid vector of the invention comprises an above described nucleic acid insert operably linked to an expression control sequence, in particular those described hereinafter.

Vectors typically perform two functions in collaboration with compatible host cells. One function is to facilitate the cloning of the edg gene, i.e., to produce useable quantities of the nucleic acid (cloning vectors). The other function is to provide for replication and expression of the gene constructs in a suitable host, either by maintenance as an extrachromosomal element or by integration into the host chromosome (expression vectors). A cloning vector comprises the DNAs as described above, an origin of replication or an autonomously replicating sequence, selectable marker sequences, and optionally, signal sequences and additional restriction sites. An expression vector additionally comprises expression control sequences essential for the transcription and translation of the edg gene. Thus, an expression vector refers to a recombinant DNA construct, such as a plasmid, a phage, recombinant virus or other vector that, upon introduction into a suitable host cell, results in expression of the cloned DNA. Suitable expression vectors are well known in the art and include those that are replicable in eukaryotic and/or prokaryotic cells.

Most expression vectors are capable of replication in at least one class of organisms but can be transfected into another organism for expression. For example, a vector is cloned in *E. coli* and then the same vector is transfected into yeast or mammalian cells even though it is not capable of replicating independently of the host cell chromosome. DNA may also be amplified by insertion into the host genome. However, the recovery of the genomic edg gene is more complex than that of exogenously replicated vector because restriction enzyme digestion is required to excise the gene. DNA can be amplified by PCR and directly transfected into the host cells without any replication component.

Advantageously, expression and cloning vectors contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g., ampicillin, neomycin, methotrexate or tetracycline, complement auxotrophic deficiencies, or supply critical nutrients not available from complex media.

Suitable selectable markers for mammalian cells are those that enable the identification of cells competent to take up the edg gene, such as dihydrofolate reductase (DHFR, methotrexate resistance), thymidine kinase, or genes conferring resistance to G418 or hygromycin. The mammalian cell transfectants are placed under selection pressure in which only those transfectants that are uniquely adapted to survive are those which have taken up and are expressing the marker.

Expression and cloning vectors usually contain a promoter that is recognized by the host organism and is operably linked to the edg gene. Suitable promoters may be inducible or constitutive. The promoters are operably linked to the edg gene by removing the promoter from the source DNA by restriction enzyme digestion and inserting the isolated promoter sequence into the vector. Both the native edg promoter sequence and many heterologous promoters may be used to direct amplification and/or expression of an edg. However, heterologous promoters are preferred, because they generally allow for greater transcription and higher yields of EDG as compared to native edg promoter.

Promoters suitable for use with prokaryotic hosts include, for example, the β-lactamase and lactose promoter systems, alkaline phosphatase, a tryptophan (trp) promoter system and hybrid promoters such as the tac promoter. Their nucleotide sequences have been published thereby enabling the skilled worker to ligate them to the edg gene using linkers or adaptors to supply any required restriction sites. Promoters for use in bacterial systems will also generally contain a Shine-Dalgarno sequence operably linked to the edg gene.

The various DNA segments of the vector DNA are operably linked, i.e., they are contiguous and placed in a functional relationship to each other. Construction of vectors according to the invention employs conventional ligation techniques. Isolated plasmids or DNA fragments are cleaved, tailored and religated in the form desired to generate the plasmids required. If desired, analysis to confirm correct sequences in the constructed plasmids is performed in a manner known in the art. Suitable methods for constructing expression vectors, preparing in vitro transcripts, introducing DNA into host cells, and performing analyses for assessing edg expression and function are known to those skilled in the art. Gene presence, amplification and/or expression may be measured in a sample directly, for example, by conventional Southern blotting, northern blotting to quantitate the transcription of mRNA, dot blotting (DNA or RNA analysis), in situ hybridization, using an appropriately labeled probe based on a sequence provided herein, binding assays, immunodetection and functional assays.

Suitable methods for manipulation of polynucleotides include those described in a variety of references, including, but not limited to, *Molecular Cloning: A Laboratory Manual*, 2nd Ed., Vol. 1–3, eds. Sambrook et al. Cold Spring Harbor Laboratory Press (1989); and *Current Protocols in Molecular Biology*, eds. Ausubel et al., Greene Publishing and Wiley-Interscience: New York (1987) and periodic updates. Those skilled in the art will readily envisage how these methods may be modified, if desired.

The invention further provides host cells capable of producing edg and heterologous (foreign) polynucleotides encoding said receptor. The nucleic acids of the invention can be expressed in a wide variety of host cells, e.g., those mentioned above, that are transformed or transfected with an appropriate expression vector. EDG proteins (or a portion thereof) may also be expressed as fusion proteins. Recombinant cells can then be cultured under conditions whereby the protein(s) encoded by the particular edg is (are) expressed.

Suitable prokaryotes include eubacteria, such as Gram-negative or Gram-positive organisms, such as *E. coli*, e.g., *E. coli* K-12 strains, DH5α and HB101, or bacilli. Further host cells suitable for edg-encoding vectors include eukaryotic microbes such as filamentous fungi or in a preferred embodiment, yeast, e.g., *Saccharomyces cerevisiae*.

The advantage of a yeast system is that yeast contain few G-protein coupled receptors and it is therefor a simple task to show that the response of the EDG receptor to a particular phospholipid is dependent on the expression of the receptor since it is expressed from a galactose inducible promoter. This is in contrast to mammalian cells in which identity and distribution of LPA and other glycerophospholipids receptors is unclear. The results show that EDG-2 specifically responds to LPA. EDG-2 does not respond to other lysophospholipids or to diacyl-glycerophospholipids, in particular phosphatidic acid (PA) or to the related lipid messenger sphingosine-1-phosphate (SPP).

Higher eukaryotic cells include insect, amphibian and vertebrate cells, or mammalian cells. The methods for expressing proteins of interest in Sf9 cells are known in the art and are described in, for example *Current Protocols in Molecular Biology*, eds. Ausubel et al., Greene Publishing and Wiley-Interscience: New York (1987) and references therein. In recent years, propagation of vertebrate cells in culture (tissue culture) has become a routine procedure. The host cells referred to in this application comprise cells in in vitro culture as well as cells that are within a host animal.

Host cells are transfected or transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique, by electroporation or by lipofectin-mediated transfection. Numerous methods of transfection are known to the skilled worker in the field. Successful transfection is generally recognized when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press).

Transfected or transformed cells are cultured using media and culturing methods known in the art, preferably under conditions whereby the particular edg is expressed. Suitable culturing media are either commercially available or readily prepared.

The edg gene is ligated into a vector, and introduced into suitable host cells to produce transformed cell lines that express the edg gene. The resulting cell line can then be produced in amounts sufficient for reproducible qualitative and quantitative analysis of the effects of a receptor-specific agonist, antagonist or allosteric modulator. The transfected cells can then be employed in an drug screening assay provided hereinafter. Such drugs are useful in diseases associated with pathogenesis of LPA. Particularly useful for assessing the specific interaction of compounds with an EDG receptor are stably transfected cell lines expressing the EDG.

Cells expressing EDG polypeptides are useful for identifying substances that bind to a specific EDG. Identification of substances that bind to a specific EDG may be achieved by assessing the ability of a test compound to inhibit the binding of labeled ligand or analog thereof Another method for identification of such substances involves assessing the ability of a test compound to inhibit specific antibody binding to an EDG.

Cells expressing EDG polypeptides are also useful for elucidating the signal transduction pathways to which EDG is coupled. By "signal transduction pathway" is meant the sequence of events that involves the transmission of a message from a cell-surface receptor to the cytoplasm. The signal will ultimately cause the cell to perform a particular function.

Thus, host cells expressing an EDG are also useful for drug screening and it is an object of the present invention to provide a method for identifying a compound or signal which modulates the activity of the EDG. The method includes exposing cells containing heterologous edg, wherein said cells produce functional EDG, to at least one compound or signal whose ability to modulate the activity of said EDG is sought to be determined. The cells are then monitored for changes caused by the modulation. Such an assay enables the identification of agonists, antagonists and allosteric modulators of EDG.

In a further aspect, the invention relates to an assay for identifying compounds that modulate the activity of any of the EDG family of receptors. The assay comprises the steps of:

contacting cells expressing an active EDG and containing heterologous edg with at least one compound to be tested for its ability to modulate the activity of said receptor, and analyzing cells for a difference in second messenger level or receptor activity.

Additionally, to determine the specificity of the compound for a particular member of the EDG family of receptors, the assay can further comprise the steps of:

contacting cells expressing one of the other EDG receptors, or the PSP-24 receptor and containing heterologous edg with the same compound tested above, and analyzing cells for a difference in second messenger level or receptor activity.

If the compound only effects receptor activity in one EDG family member, it is more specific, and may be preferable for certain therapeutic purposes, for example, to reduce the likelyhood of undesired biological effects.

In particular, the invention covers an assay for identifying compounds that modulate the activity of EDG's, said assay comprising:

contacting cells expressing an active EDG and containing heterologous edg with at least one compound to be tested for its ability to modulate the activity of said receptor, and monitoring said cells for a resulting change in second messenger activity.

The results obtained in these assays are compared to an assay suitable as a negative control.

Assay methods generally require comparison to various controls. A change in receptor activity or in second messenger level is "induced" by a test compound if such an effect does not occur in the absence of the test compound. An effect of a test compound on the receptor of the invention is "mediated" by the receptor if this effect is not observed in cells that do not express the receptor or express decreased amounts of the receptor.

As used herein, a compound or signal that modulates the activity of an EDG receptor refers to a compound or signal that alters the response pathway mediated by the EDG within a cell (as compared to the absence or decreased amount of said EDG). A response pathway is activated by an extracellular stimulus, resulting in a change in second messenger concentration or enzyme activity, or resulting in a change of the activity of a membrane-bound protein, such as a receptor or ion channel. A variety of response pathways can be utilized, including but not limited to, the adenylate cyclase response pathway, the phospholipase C/intracellular calcium ion response pathway or a response pathway involving activation of Ras or Rho.

Apoptosis represents another important response pathway that may be modulated by EDG agonists or antagonists. Suitable indications for therapeutic use of EDG agonists or antagonists that result in modulation of apoptotic pathways include, but are not limited to, ischemic heart disease, tumors, viral diseases such as HIV infection, neurodegenerative disorders, inflammatory bowel disease, hair loss, and rejection of organ transplants.

Thus EDG expressing cells may be employed for the identification of compounds, particularly low molecular weight molecules capable of acting as LPA agonists or antagonists. Within the context of the present invention, an agonist refers to a molecule that is capable of interacting with one or more EDG's, thus mimicking the action of LPA. In particular, an LPA agonist is characterized by its ability to interact with EDG-2, thereby increasing or decreasing the stimulation of a response pathway within a cell. For example, an agonist increases or decreases a measurable parameter within the host cell, such as the concentration of a second messenger or modulation of apoptosis.

By contrast, in situations where it is desirable to decrease the activity of an EDG, antagonists are useful. Liliom et al. (1996) *Molec. Pharmacol.* 50:616–623; Bittman et al. (1996) *J. Lipid Res.* 37:391–398. Within the context of the present invention, an antagonist refers to a molecule that is capable of interacting with an EDG, but which does not stimulate a response pathway within a cell. In particular, LPA antagonists are generally identified by their ability to interact with EDG-2, and thereby reduce the ability of the natural ligand to stimulate a response pathway within a cell, e.g., by interfering with the binding of LPA to EDG-2 or by inhibiting other cellular functions required for the activity of EDG-2. For example, in a suitable assay, e.g., an assay involving suitable eukaryotic cells expressing EDG-2, a LPA antagonist is capable of modulating the activity of EDG-2 such that the ability of the natural ligand to activate the map kinase pathway is reduced. Yet another alternative to achieve an antagonistic effect is to rely on overexpression of antisense edg-2 RNA. Preferred is an agonist or antagonist selectively acting on EDG-2.

An allosteric modulator of an EDG interacts with the receptor protein at another site than that recognized by any one of its particular ligands, thus acting as agonist or antagonist. Therefore, the screening assays described herein are also useful for detecting an allosteric modulator of a receptor of the invention. For example, an allosteric modulator acting as agonist may enhance the specific interaction between EDG-2 and LPA. For instance, if an allosteric modulator acts as an antagonist, it may interact with the receptor protein in such a way that binding of the agonist is functionally less effective. Examples include local anesthetics such as procaine, lidocaine, dibucaine and tetracaine.

An in vitro assay for a LPA agonist or antagonist may require that an EDG is produced in sufficient amounts in a functional form using recombinant DNA methods. An assay is then designed to measure a functional property of the EDG, e.g., interaction with LPA. Production of EDG is regarded as occurring in sufficient amounts if activity of the receptor results in a measurable response.

For example, mammalian cells (available, e.g., from the American Tissue Type Culture Collection) are grown in appropriate culture medium. An EDG expression plasmid is transiently transfected into the cells, e.g., by calcium-phosphate precipitation. Ausubel, F.M. et al. (1993). Cell lines stably expressing the EDG may be generated, e.g., by lipofectin-mediated transfection with EDG expression plasmids and a plasmid comprising a selectable marker gene. Southern and Berg (1982) *J. Mol. Appl. Genet* 1:327–341. Cells surviving the selection are isolated and grown in the selection medium. Resistant clonal cell lines are analyzed, e.g., for immunoreactivity with EDG-specific antibodies or by assays for EDG functional responses following agonist addition. Cells producing EDG are used in a method for detecting compounds binding to EDG or in a method for identifying an EDG ligand agonist or antagonist.

Compound bound to the target EDG may modulate functional properties of EDG and may thereby be identified as an EDG ligand agonist or antagonist in a functional assay. Functional assays are used to detect a change in the functional activity of EDG's, for instance, as a result of the interaction of the compound to be tested with an EDG. A functional response is a change (difference) in the concentration of a relevant second messenger influenced by the receptor of the invention within cells expressing a functional EDG (as compared to a negative control). Those of skill in the art can readily identify an assay suitable for detecting a change in the level of an intracellular second messenger indicative of the expression of active EDG-2 (functional assay). Examples include cAMP assays (see, e.g., Nakajima et al. (1992) *J. Biol. Chem.* 247:2437–2442); Tigyi et al. (1996) *J. Neurochem.* 66:549–558) measuring changes in inositol 1,4,5-triphosphate levels (Tigyi et al. (1996) *J. Neurochem.* 66:537–548), measuring Cl$^-$ ion efflux (Postma et al. (1996) *EMBO J.* 15:63–72; Watsky (1995) Am. J. Physiol. 269:C1385–C1393), or measuring changes in intracellular Ca$^{2+}$ levels (Tigyi et al. (1996) *J. Neurochem.* 66:537–548).

More specifically, according to the invention, a method for detecting a LPA agonist comprises the steps of (a) exposing a compound to EDG-2 coupled to a response pathway, under conditions and for a time sufficient to allow interaction of the compound with EDG-2 and an associated response through the pathway, and (b) detecting an increase or decrease in the stimulation of the response pathway resulting from the interaction of the compound with EDG-2, relative to the absence of the tested compound and therefrom determining the presence of a LPA agonist.

A method for identifying a LPA antagonist comprises the steps of (a) exposing a compound in the presence of a known LPA agonist to EDG-2 coupled to a response pathway, under conditions and for a time sufficient to allow interaction of the agonist with the receptor and an associated response through the pathway, and (b) detecting an inhibition of the stimulation of the response pathway induced by the agonist, said inhibition resulting from the interaction of the compound with EDG-2, relative to the stimulation of the response pathway by the LPA agonist alone and determining therefrom the presence of a LPA antagonist. Inhibition may be detected if the test compound competes with the LPA agonist for EDG-2. Compounds which may be screened utilizing such a method include, but are not limited to, blocking antibodies specifically binding to EDG-2. Furthermore, such an assay is useful for the screening for compounds interacting with LPA. In this case, the agonistic effect is neutralized or reduced, e.g., by binding of the test compound to the agonist, thus affecting agonist interaction with the receptor. Examples are soluble EDG-2 fragments comprising part or all of the ligand binding domain.

Preferentially, interaction of an agonist or antagonist with EDG-2 denotes binding of the agonist or antagonist to said EDG-2.

As employed herein, conditions and times sufficient for interaction of an LPA agonist or antagonist candidate with the receptor will vary with the source of the receptor, however, conditions generally suitable for binding occur between about 4° C. and about 40° C., preferably between about 4° C. and about 37° C., in a buffer solution between 0 and 2 M NaCl, preferably between 0 and 0.9 M NaCl, with 0.1 M NaCl being particularly preferred, and within a pH range of between 5 and 9, preferably between 6.5 and 8. Sufficient time for the binding and response will generally be between about 1 ms and about 24 h after exposure.

Within one embodiment of the present invention, the response pathway is a membrane-bound Map Kinase pathway, and, for an agonist, the step of detecting comprises measuring a reduction or increase, preferably a reduction, in lacZ production by the membrane-bound response pathway, relative to the lacZ production in the relevant control setup. For the purpose of the present invention, it is preferred that the reduction or increase in lacZ production be equivalent or greater than the reduction or increase induced by LPA applied at a concentration corresponding to its IC$_{50}$ value. For an antagonist, the step of detecting comprises measuring in the presence of the antagonist a smaller LPA-induced decrease or increase in lacZ production by the membrane-bound response pathway, as compared to the lacZ production in the absence of the antagonist. The measurement of lacZ may be performed after cell destruction or by a lacZ sensitive molecular probe loaded into the cell.

Yeast contains multiple MAP kinase cascades that are functionally analogous to the Mitogen Activated Protein Kinase (MAPK) cascade in mammalian systems (Brewster, J. L., et al. (1993) *Science* 259, 1760–1763; Irie, K., et al. (1993) *Mol. Cell. Biol.* 13, 3076–3083; Neiman, A. M., and Herskowitz, I. (1993) *Trends Genet.* 9, 390–394; Chang, E. C., et al. (1994) *Cell* 79, 131–141). A schematic of the S. cerevisiae pheromone response pathway and the relevant genetic components are shown in FIG. 1. The parental yeast strain, SY2069, contains the FUS1 promoter fused to lacZ and HIS3 integrated into different chromosomal loci and carries the far1-bad allele. The FAR1 gene product is required for cell cycle arrest following exposure to mating pheromone (see FIG. 1). By deleting this gene, the cells are able to grow in the presence of MAP kinase activation. In addition, a null mutation in the SST2 gene was created because it has been previously reported that the Sommatostatin receptor can efficiently couple to the endogenous yeast heterotrimeric G-protein after mutationally inactivating the SST2 gene (Price, L. A., Kajkowski, E. M., Hadock, J. R., Ozenberger, B. A., and Pausch, M. H. (1995) *Mol. Cell. Biol.* 15(11), 6188–6195). SST2 encodes a GTPase activating protein (GAP) for the GPA1 gene product, the Gα subunit required for mating pheromone signal transduction. The effect of inactivating SST2 is that Gpa1 remains in the GTP-bound state longer and thus permits signaling through the βγ dimer to proceed at a higher rate, resulting in a higher signal from the receptor.

Further cell-based screening assays can be designed, e.g., by constructing cell lines in which the expression of a reporter protein, i.e., an easily assayable protein, such as β-galactosidase, chloramphenicol acetyltransferase (CAT) or luciferase, is dependent on the function of an EDG. The resulting DNA construct comprising the enzyme DNA is stably transfected into a host cell. The host cell is then transfected with a second DNA construct containing the edg gene operably linked to additional DNA segments necessary for the expression of the receptor.

Also encompassed by methods of the present invention is the use of the EDG family of receptors in an expression vector for radioligand binding assays, such as that described in Price, L. A., et al. (1996) Mol. Pharmacol. 50(4), 829–837. Such methods can be used for detecting compounds that compete with known EDG binding ligands for binding to the EDG related receptors. For example, first labeled 18:1 lysophosphatidic acid ligand is introduced to a sample containing yeast cells expressing EDG-2 receptor to allow binding of the 18:1 LPA to the EDG-2 receptor. Next, a composition to be tested for its ability to modulate the interaction of 18:1 LPA and its receptor is introduced to the yeast cell. Finally, the yeast sample is evaluated for an increase or decrease in the amount of labeled agonist bound to the yeast cell or membranes purified from the yeast cell. Methods of labeling compounds, and labels themselves, are known in the art and include, but are not limited to, radioisotopes, enzymes, fluorescent compounds, chemiluminescent compounds, bioluminescent compounds, substrate cofactors and inhibitors. See, for examples of patents teaching the use of such labels, U.S. Pat. Nos. 3,817,837; 3,850,752; 3,939,350; 3,996,345; 4,277,437; 4,275,149; and 4,366,241. By these methods, one can identify the presence of an EDG related receptor modulator, such as an antagonist, inverse agonist or agonist.

The edg gene family is useful for a variety of studies. These include, but are not limited to, testing LPA analogs for agonistic/antagonistic activity and for EDG-2 specificity when compared to other EDG family members; dissecting the molecular signal transduction mechanism, analyzing receptor-ligand interactions by site-directed mutagenesis; determining the levels and distribution of the receptors; cloning related receptors; and determining the mechanism of tissue-specific responses to LPA and other EDG family ligands.

Recently, it has been discovered that a lysophospholipid effects Candida adherence in vitro. Prakobphol, A., et al. "Plamitoyl carnitine, a lysophospholipase-transacylase inhibitor, prevents Candida adherence in vitro," FEMS Microbiol Lett (1997) 151:89–94. By identifying a lysophosphatidic acid receptor in Candida, and inserting that receptor into an assay of the present invention, one can screen for potential anti-fungal agents that modulate the interaction of LPA and such a receptor.

Methods of the present invention can be used to identify an LPA receptor from a heterologous fungal species, such as Candida. For example, one can a) contact recombinant host cells, modified to contain a fragment of at least 18 consecutive nucleotides of DNA selected from the genomic library of a chosen fungal species, which is operably linked to control sequences for expression, with LPA. Next, one can b) analyze the cells for a change in functional response to said LPA. Finally, one can repeat steps a) and b) with different fragments from the genomic library of the heterologous fungus until a fragment is identified that evokes a change in functional response upon treatment with LPA.

The following examples are provided to illustrate but not limit the invention.

EXPERIMENTAL

The following abbreviations, used in the experimental section and throughout the specification, are herein set forth: LPA (lysophosphatidic acid), LPE (lysophosphatidylethanolamine), LPS (lysophosphatidlyserine), LPC (lysophosphatidlycholine), LPG (lysophosphatidlyglycerol), PA (phosphatidic acid), PE (phosphatidylethanolamine), PS (phosphatidylserine), PC (phosphatidylcholine), PG (phosphatidylglycerol), Sph-1-P (shingosine-1-phosphate), BBS (Bicarbonate buffered saline).

EXAMPLE 1

Construction of the EDG-1, EDG-2, EDG-3, EDG-4 and EDG-5 Expression Plasmids and Expression in Yeast SY2069 (Mata, far1-bad3, HIS3::pFUS1::HIS3, mfa2-Δ1::pFUS1::lacZ, ura3, leu2, ade1, arg4, trp1) was used to derive an sst2⁻ strain for subsequent studies. SST2 was disrupted using pBC14 (Dohlman, H. G., et al. (1996) *Mol. Cell. Biol.* 16(9), 5194–5209). pBC14 was digested with NcoI and transformed into SY2069 by lithium acetate using the URA3 gene for selection. Ura⁺ colonies were grown in non-selective media (YEPD) and plated onto media containing 5-Flouro-orotic Acid (5-FOA, Sigma). The resultant 5-FOA resistant isolates were tested for the supersensitive phenotype by assaying lacZ activity in response to α-factor (data not shown). One sst2⁻ strain was named JEY5 and used in all subsequent studies. Yeast were grown in SC+2% Galactose or 2% Glucose media lacking Uracil.

Construction of EDG-2 Expression Plasmid and Expression in Yeast: The EDG-2 coding region was amplified by RT-PCR using Pfu DNA polymerase under conditions described by the supplier (Stratagene). The template for RT-PCR was cDNA (5 ng) that was reverse transcribed from human fetal brain total RNA (Clontech) using SuperScript II Reverse Transcriptase as described by the supplier (Gibco BRL). 1 μM each of the following primers, FP; 5'-GCGATAGGATCCATCATGGCTGCCATCTCTAC TTC-3' (SEQ ID NO. 2) and RP; 5'-GCGATACTCGAGCTAAACCACAGAGTGATCA TTGC-3' (SEQ ID NO. 3), were used for RT-PCR. Oligonucleotide Synthesis and DNA Sequencing: PCR primers and DNA sequencing primers were synthesized by the phosphoramidite method with an Applied Biosystems model 394 synthesizer, purified by polyacrylamide gel electrophoresis and desalted on Sep-Pak $C_{18}$ cartridges (Waters Associates, Milford, Mass.). The edg-2 cDNA was sequenced in pYEUra3 by the dideoxy chain termination method using the T7 Sequenase7-deaza-dGTP sequencing kit as described by the supplier (Amersham Life Science). The primers were designed based on the human edg-2 cDNA sequence submitted to Genbank by Zondag and Moolenaar (accession no. Y09479) and included restriction site extensions for subcloning into the pYEUra3 vector (Stratagene). This placed the cDNA under the control of a galactose-inducible promoter (UASgal). The resulting plasmid was used to transform JEY5 by the lithium acetate method.

Construction of EDG-1, EDG-3, EDG-4 and EDG-5 Expression Plasmid and Expression in Yeast: The other EDG Expression Plasmids were prepared by the same method described above for EDG-2, except that the coding regions were amplified by RT-PCR using the following primers, respectively:

EDG-1:FP; 5'-GCGCGGGATCCACCATGGGGCCCAC-
    CAGCGTCCCG-3'    (SEQ ID NO.10 )

RP;5'-GCGCGGTCGACGGAAGAAGAGTTGA
    CGTTTCC-3'    (SEQ ID NO. 11 )

EDG-3:FP; 5'-GCGCGGGATCCACCATGGCAACTGC-
    CCTCCCG-3'    (SEQ ID NO. 12)

RP;5'-GCGCGGTCGACTCAGTTGCAGAAGAT
    CCCATTC-3'    (SEQ ID NO. 13)

EDG-4:FP;5'-ATCAGCGGATCCACCATGGTCAT-
    CATGGGCCAGT-3'    (SEQ ID NO. 14)

RP;5'-AGTTCACTCGAGTCAGTCCTGTTGGTTG
    GGTTG-3'    (SEQ ID NO. 15)

EDG-5:FP;5'-GCGCGGGATCCACCATGGGCGGTT-

TATACTCAGAG-3' (SEQ ID NO.16)

RP;5'-GCGCGGTCGACTCAGACCACTGTGTT (SEQ ID NO. 17).

Figure 2:
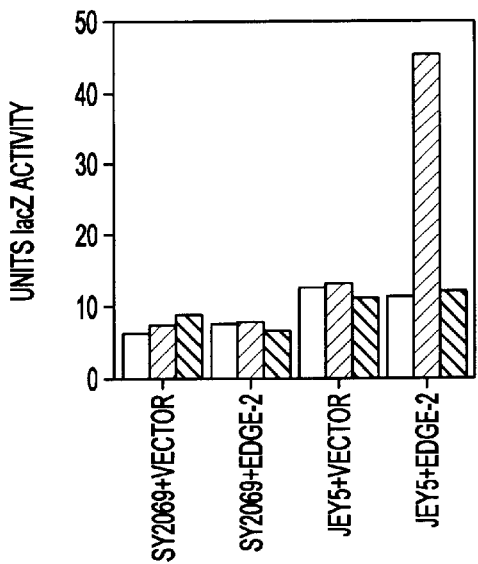
FIG. 2 is a graph depicting EDG-2-mediated stimulation of FUS1::lacZ. Yeast cells carrying the galactose-inducible edg-2 gene were grown in SC media containing either 2% galactose (filled bars) or 2% glucose (hatched bars) for seven hours in the presence of lysophosphatidic acid (LPA) or on galactose in the absence of LPA (open bars). After seven hours, the cells were assayed for β-galactosidase (lacZ) activity.

Expression of the EDG-2: To test the effects of the SST2 gene product on the edg-2 response to LPA, JEY5 (sst2Δ) expressing the EDG-2 receptor was compared to the parental SY2069 strain (SST2$^+$). FIG. 2 shows that the SST2$^+$ strain was unresponsive to LPA whereas the sst2$^-$ derivative was activated by 200 μM LPA. As a control, JEY5+EDG-2 was assayed in 2% glucose such that the GAL1 promoter would be repressed and thus not expressing the edg-2 gene (glucose repression is described in detail by Johnston, M., and Carlson, M. (1992) in *The molecular and cellular biology of the yeast Saccharomyces: gene expression* (Broach, J. R., Pringle, J. R., and Jones, E. W., eds), pp. 193–281, Cold Spring Harbor Laboratory Press, Plainview, N.Y.). lacZ assays in response to phospholipids: JEY5+pJE15 was grown on SC media containing either 2% galactose or 2% glucose lacking uracil to an approximate optical density of 0.1–0.5 prior to the addition of lipid or α-factor. LPA and other glycerophospholipids (Avanti Polar Lipids) were dissolved in chloroform and dried down under vacuum immediately prior to experiments and resuspended in BBS/EDTA (50 mM NH$_4$HCO$_3$, 104 mM NaCl, 250 mM EDTA2Na) at 1 mg/ml with sonication until the solution was clear. Sphingosine-1-phosphate (Matreya) was resuspended in ethanol/water (9:1) pH 3.0 immediately prior to use. Fatty Acid Free Bovine Serum Albumin was obtained from Sigma (St. Louis, Mo.) and used at 0.1 mg/ml in BBS/EDTA. Cells were allowed to grow for the indicated time (7 hours for dose response experiments) prior to assaying. 100 μl of yeast culture were then added to 900 μl assay buffer (per liter: 60 mM Na$_2$HPO$_4$, 40 mM NaH$_2$PO$_4$, 10 mM KCl, 0.1 mM MgSO$_4$, pH 7.0 plus 2.7 ml β-mercaptoethanol per liter) plus 50 μl 0.1%SDS+three drops Chloroform. Cells were vortexed for 10 seconds and incubated for 5 minutes at 28° C. 200 μL of 4 mg/ml o-nitrophenol-β-D-galactopyranoside (ONPG, Sigma) were added and the reaction was incubated 30 minutes at 28° C. The assay was stopped by the addition of 500 μl 1M Na$_2$CO$_3$. Color development was measured at A$_{420}$ and normalized to A$_{600}$. Units were expressed as Miller Units.

FIG. 2 shows that the induction of lacZ activity is dependent on 1) the pYEUra3-Edg2 plasmid being present in the yeast cell, 2) the yeast cell containing the pYEUra3-Edg2 plasmid being grown on the sugar galactose such that the UASgal promoter which drives the expression of the Edg2 gene is induced and 3) lysophosphatidic acid being present.

Figure 3A:
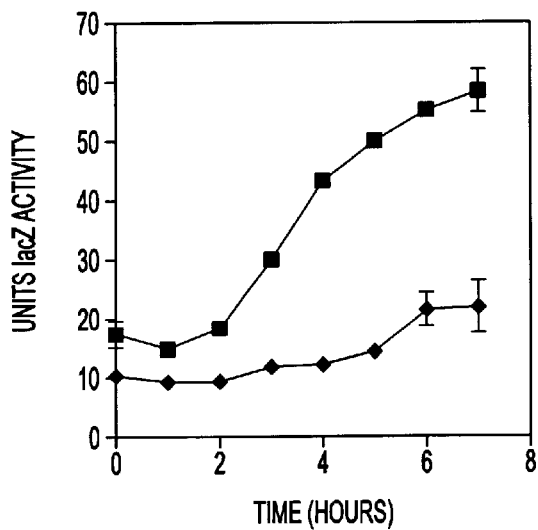
FIGS. 3A and 3B are graphs depicting the stimulation by LPA of FUS1::lacZ activity in cells expressing EDG-2 in a time and dose dependent manner, respectively. 3A: Yeast cells carrying edg-2 (■) or empty vector (♦) were grown in synthetic complete media (S. C.)+2% galactose for the indicated time prior to assaying β-galactosidase activity. 3B, Yeast cells carrying edg-2 were grown for seven hours at the indicated dose of LPA.
Figure 3B:
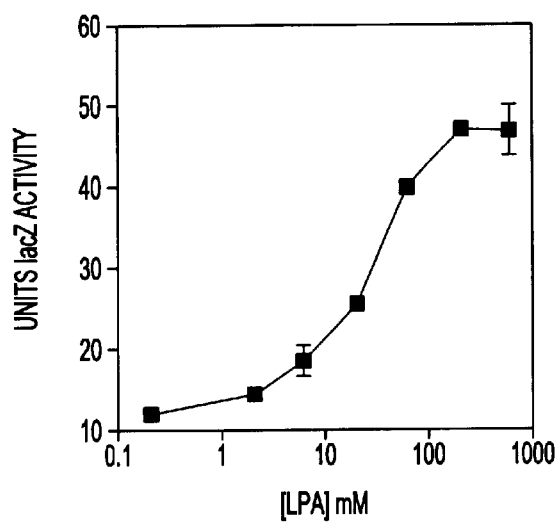

To further characterize the LPA response to EDG-2, the time and dose dependency of LPA activation was tested. As seen in FIG. 3A, LPA results in a time-dependent increase in lacZ activity as compared to vector control with a maximal four-fold stimulation of activity at 7 hours. The dose response of EDG-2 to LPA is shown in FIG. 3B (E.C.50=20 μM–30 μM). LPA concentrations above 600 μM could not be tested due to toxicity. However, the dose response curve can been seen to plateau suggesting that maximal activity has been reached. This toxicity was seen in other glycerophospholipids tested at 200 μM (see below). However, the response to LPA was significantly above the vector control suggesting that EDG-2 confers LPA responsiveness upon yeast. LPA resuspended in BBS/EDTA+fatty acid free albumin showed the same activity as did freely soluble LPA (data not shown and see below).

The results support that the expression of EDG-2 in yeast faithfully reconstitutes many of the key properties of an LPA receptor.

EXAMPLE 2

EDG-2 Responds Selectively to LPA and not to Other Lysophospholipids or to Corresponding Diacyl-glycerophospholipids Yeast does not have endogenous receptors for glycerphospholipids such as LPA. Therefor, yeast represented an excellent naive system to evaluate the agonist binding specificity of EDG-2. Lysophosphatidylethanolamine (LPE), -serine (LPS), -glycerol (LPG) and -choline (LPC) and Sphingosine-1-phosphate (SPP) were tested over the same dose range as LPA.

Figure 4:
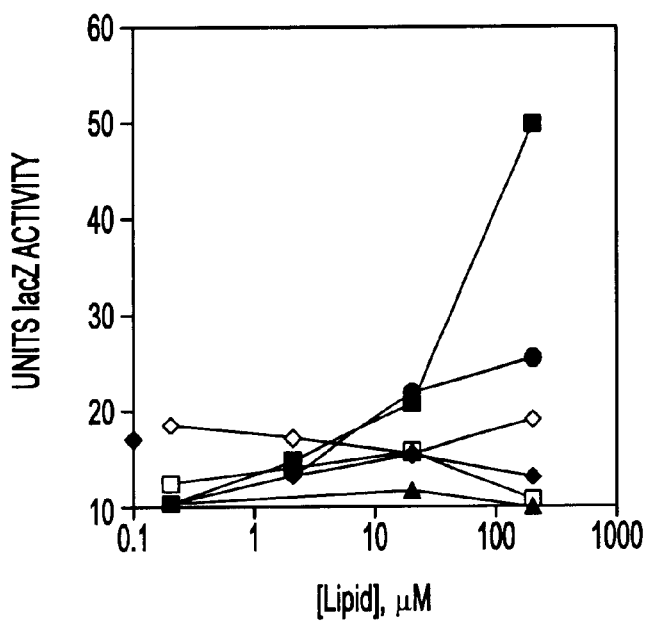
FIG. 4 is a graph depicting the specific activation by LPA, but not other related lysophospholipids or Sphingosine-1-phosphate (SPP), of FUS1::lacZ. Yeast cells carrying edg-2 were grown in S. C.+2% galactose in the presence of LPA (■), LPC (♦), LPE (●), LPG (▲), LPS (□) or Sph-1-P (○) at the indicated concentrations for seven hours. All lyso-glycerophospholipid were resuspended in BBS/EDTA+1 mg/ml fatty acid free bovine serum albumin to enhance solubility.
Figure 5:
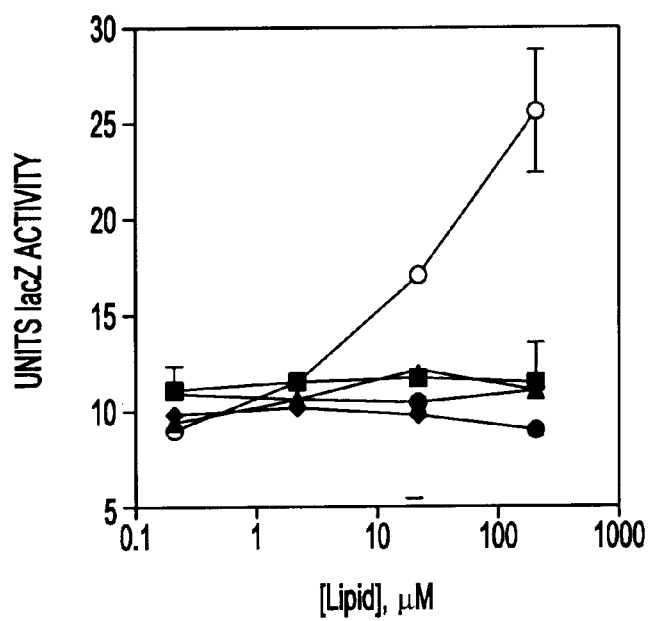
FIG. 5 is a graph depicting the specific activation of FUS1::lacZ by LPA, but not Diacyl-glycerophospholipids. Yeast cells were cultured in S. C.+2% galactose in the presence of PA (■), PC (♦), PE (●), PG (▲) PS (□) or LPA (○) at the indicated concentration for seven hours. All diacyl-glycerophospholipid were resuspended in BBS/EDTA+1 mg/ml fatty acid free bovine serum albumin to enhance solubility.

The results are consistent with EDG-2 being a functional, specific LPA receptor. As seen in FIG. 4, no other lyso-glycerolphospholipid or Sphingosine-1-phosphate activated EDG-2 as well as did LPA at concentrations up to 200 μM, the highest concentration tested due to toxicity. The results of a similar experiment testing the effects of the diacyl-glycerophospholipids are seen in FIG. 5. In this experiment, no diacyl-glycerophospholipid significantly activated EDG-2 except phosphatidic acid (PA). However, the activity of PA may be due to contaminating LPA as determined by HPLC (data not shown).

EXAMPLE 3

Acyl-chain Length Dependency of EDG-2 Activity by LPA

Due to the apparent specificity of EDG-2 for LPA, the dependency of the acyl-chain length of the LPA molecule on EDG-2 activation was also determined. Six forms of LPA were tested: 24:1, 18:1 (Oleoyl), 18:0 (Stearoyl), 16:0 (Palmitoyl), 14:0 (Myristoyl) and 6:0 (Caproyl). The experiment was carried out as described in Example 2, above, using the four forms of LPA.

Figure 6:
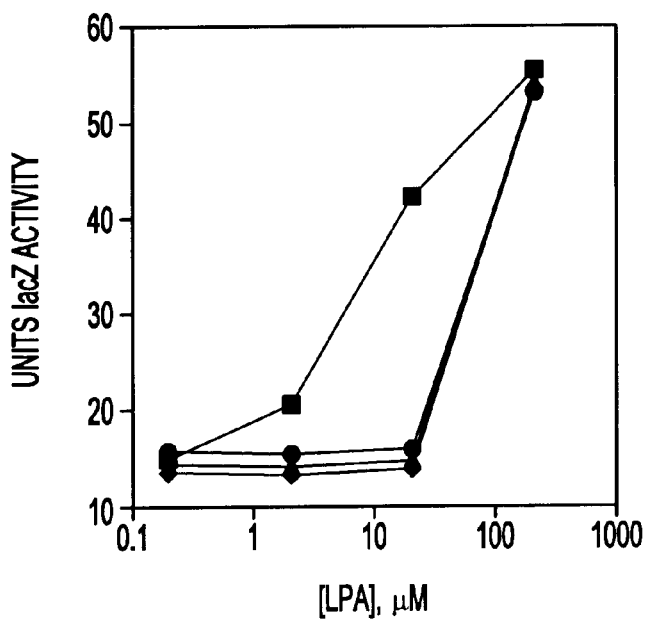
FIG. 6 is a graph depicting the effect of the fatty acid side-chain of LPA on activation of FUS1::lacZ. Yeast cells expressing EDG-2 were cultured in S. C.+2% galactose in the presence of 18:1 oleoyl LPA (■), 18:0 steroyl LPA (♦), 16:0 palmitoyl LPA (●) or 14:0 (▲) at the indicated concentration for seven hours. The numerical representation refers to the chain length and degree of saturation. All forms of LPA were resuspended in BBS/EDTA+1 mg/ml fatty acid free bovine serum albumin to enhance solubility.

FIG. 6 shows that those LPA molecules containing 16 or 18 carbons activated EDG-2. This experiment was repeated with the LPA analogs suspended in 0.1 mg/ml fatty acid free BSA with similar results (data not shown).

EXAMPLE 4

LPA in a Liposomal Formulation is Effective in EDG-2 Activation

To test the effects of presenting LPA to the yeast cells as a liposome rather than as freely soluble LPA or bound to albumin, liposomes were formed with either phosphatidylcholine or phosphatidylglycerol. To formulate the liposomes, LPA and dioleoyl-phosphatidylcholine or 1-palmitoyl-2-oleoyl-phosphatidylglycerol were mixed at a weight ratio of 1:9 (LPA:PC or PG) in Chloroform solution, dried under vacuum (Savant) and resuspended in BBS/EDTA to a total lipid concentration of 10 mg/ml (LPA concentration =1 mg/ml). The resultant opaque suspension was sonicated until the solution was clear (approximately 10 minutes, Lab Supplies Co., Hicksville, NY). The liposome size ranged from 50 nm to 80 nm as determined on a Coulter N4 Plus Particle Sizer. (Coulter).

Figure 7:
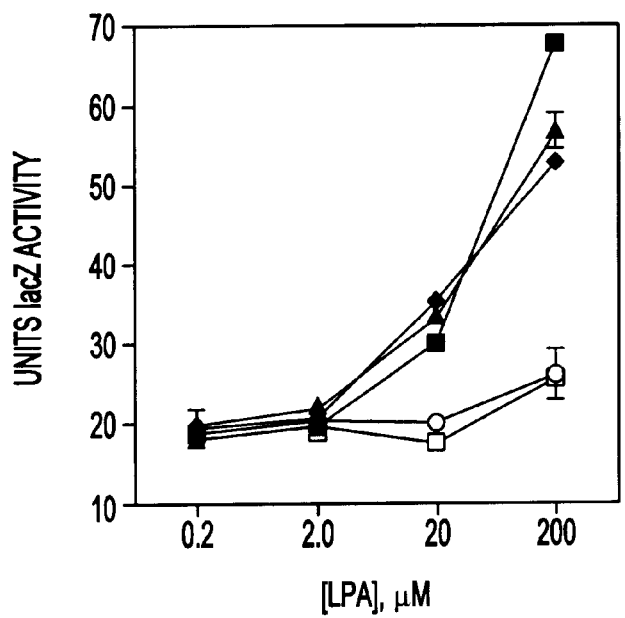
FIG. 7 is a graph depicting the activation of FUS1::lacZ by LPA presented either as a liposomal formulation or as freely soluble LPA. Yeast cells carrying EDG-2 were culture in S. C.+2% galactose in the presence of freely soluble LPA (■), LPA+PC liposomes (♦), PC alone (○), LPA+PG liposomes (▲) or PG alone (□). Note that the concentration of lipid reflects only the LPA component of the liposome.

FIG. 7 shows that LPA-containing liposomes showed equivalent activity towards EDG-2 as did freely soluble LPA. Phosphatidylcholine and phosphatidylglycerol as liposome preparations gave no activity on their own (FIG. 4). These results support that the form in which LPA is presented does not significantly effect its ability to activate EDG-2; albumin-bound, freely soluble and liposomal formulations of LPA all activated EDG-2 with equal efficacy.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

---

We claim:

1. A method for detecting compounds of interest which act as inverse agonists of LPA in its interaction with EDG-2, comprising the steps of
   a) exposing a compound and LPA to host fungal cells transgenically expressing the EDG-2 receptor (SEQ ID NO. 20), wherein the EDG-2 receptor is coupled to a response pathway through an interaction with the endogenous G-protein of the host fungal cell, under conditions and for a time sufficient to allow interaction of LPA with the EDG-2 receptor and an associated response through the pathway; and
   b) detecting an increase or a decrease in a product of the response pathway resulting from the interaction of the compound with the EDG-2 receptor, relative to the absence of the tested compound, and therefrom determining the presence of an antagonist or an allosteric modulator.

2. The method of claim 1 wherein the host fungal cells are yeast cells.

3. The method of claim 1 wherein the product of the functional response is a second messenger selected from the group consisting of cAMP, inositol 1,4,5 triphosphate, $Cl^-$ ion, and $Ca^{+2}$ ion.

4. A method for identifying compounds of interest which modulate the activity of EDG-2 receptor comprising the steps of:
   a) contacting recombinant host fungal cells, modified to contain the DNA of SEQ. ID.No.1 which is operably linked to control sequences for expression, wherein the EDG-2 receptor is coupled to a response pathway through an interaction with the endogenous G-protein of the host fungal cell, with at least one compound of interest, and
   b) detecting an increase or a decrease in a product of the response pathway resulting from the interaction of the compound with the EDG-2 receptor, relative to the absence of the compound, wherein the product is a second messenger selected from the group consisting of cAMP, inositol, 1,4,5 triphosphate, $Cl^-$ ion, and $Ca^{+2}$ ion, and therefrom determining the presence of an antagonist or an allosteric modulator.

* * * * *